United States Patent
Le

(10) Patent No.: US 10,300,039 B2
(45) Date of Patent: May 28, 2019

(54) FERRIC CITRATE DOSAGE FORMS

(71) Applicant: KERYX BIOPHARMACEUTICALS, INC., Boston, MA (US)

(72) Inventor: Henry Trong Le, Englewood Cliffs, NJ (US)

(73) Assignee: KERYX BIOPHARMACEUTICALS, INC., Boston, MA (US)

( * ) Notice: Subject to any disclaimer, the term of this patent is extended or adjusted under 35 U.S.C. 154(b) by 0 days.

(21) Appl. No.: 15/159,008

(22) Filed: May 19, 2016

(65) Prior Publication Data

US 2016/0263075 A1 Sep. 15, 2016

Related U.S. Application Data

(62) Division of application No. 13/255,326, filed as application No. PCT/US2010/042788 on Jul. 21, 2010, now Pat. No. 9,387,191.

(60) Provisional application No. 61/227,124, filed on Jul. 21, 2009.

(51) Int. Cl.
*A61K 9/20* (2006.01)
*A61K 31/295* (2006.01)

(52) U.S. Cl.
CPC .......... *A61K 31/295* (2013.01); *A61K 9/2013* (2013.01); *A61K 9/2054* (2013.01); *A61K 9/2059* (2013.01); *A61K 9/2077* (2013.01); *A61K 9/2095* (2013.01)

(58) Field of Classification Search
None
See application file for complete search history.

(56) References Cited

U.S. PATENT DOCUMENTS

| | | | |
|---|---|---|---|
| 2,081,547 A | 5/1937 | Mattheus |
| 3,091,574 A | 5/1963 | Coletta et al. |
| 3,549,614 A | 12/1970 | Mioduszewski |
| 3,591,616 A | 7/1971 | Baldt |
| 3,873,588 A | 3/1975 | Osawa et al. |
| 4,180,567 A | 12/1979 | Herb |
| 4,689,322 A | 8/1987 | Treptow et al. |
| 4,970,079 A | 11/1990 | Hem et al. |
| 5,006,344 A | 4/1991 | Jerzewski et al. |
| 5,089,644 A | 2/1992 | Quay |
| 5,206,265 A | 4/1993 | Vidic et al. |
| 5,707,980 A | 1/1998 | Knutson et al. |
| 5,753,706 A | 5/1998 | Hsu |
| 6,174,442 B1 | 1/2001 | Geisser et al. |
| 6,180,094 B1 | 1/2001 | Sasaki et al. |
| 6,413,558 B1 | 7/2002 | Weber et al. |
| 6,495,177 B1 | 12/2002 | Vries et al. |
| 6,887,897 B2 | 5/2005 | Walsdorf et al. |
| 6,903,235 B2 | 6/2005 | Hsiao et al. |
| 7,767,851 B2 | 8/2010 | Kwok et al. |
| 8,093,423 B2 | 1/2012 | Kwok et al. |
| 8,178,709 B2 | 5/2012 | Nelson et al. |
| 8,299,298 B2 | 10/2012 | Chan et al. |
| 8,338,642 B2 | 12/2012 | Kwok et al. |
| 8,609,896 B2 | 12/2013 | Kwok et al. |
| 8,754,257 B2 | 6/2014 | Chan et al. |
| 8,754,258 B2 | 6/2014 | Kwok et al. |
| 8,846,976 B2 | 9/2014 | Kwok et al. |
| 8,901,349 B2 | 12/2014 | Kwok et al. |
| 9,050,316 B2 | 6/2015 | Chan et al. |
| 9,328,133 B2 | 5/2016 | Kwok et al. |
| 9,387,191 B2 | 7/2016 | Le |
| 9,750,715 B2 | 9/2017 | Chan et al. |
| 9,757,416 B2 | 9/2017 | Chan et al. |
| 9,889,113 B2 | 2/2018 | Chan et al. |
| 9,913,821 B2 | 3/2018 | Kwok et al. |
| 2002/0197310 A1 | 12/2002 | Hunter et al. |
| 2005/0203169 A1 | 9/2005 | Moskowitz |
| 2006/0020026 A1 | 1/2006 | Kwok et al. |
| 2006/0134225 A1 | 6/2006 | Moerck et al. |
| 2006/0134227 A1 | 6/2006 | Bortz et al. |
| 2007/0161600 A1 | 7/2007 | Helenek et al. |
| 2008/0145410 A1 | 6/2008 | Ambuhl et al. |
| 2008/0193531 A1 | 8/2008 | Hermelin et al. |
| 2008/0274210 A1 | 11/2008 | Chan et al. |
| 2009/0110722 A1 | 4/2009 | Cardoso de Vasconcelos et al. |
| 2009/0186939 A1 | 7/2009 | Chan et al. |
| 2009/0326060 A1 | 12/2009 | Chan et al. |
| 2010/0217025 A1 | 8/2010 | Kwok et al. |

(Continued)

FOREIGN PATENT DOCUMENTS

| | | |
|---|---|---|
| AU | 199854419 | 7/1998 |
| AU | 723091 | 11/2000 |
| AU | 2004213819 | 8/2005 |
| AU | 2006279333 | 3/2008 |
| AU | 2007210090 | 7/2008 |
| AU | 2007210096 | 7/2008 |
| AU | 2004213819 | 12/2009 |
| AU | 2010276242 | 9/2014 |
| CA | 2272711 | 5/1999 |
| CA | 2516471 | 8/2005 |
| CA | 2619591 | 2/2008 |
| CA | 2272711 | 4/2008 |

(Continued)

OTHER PUBLICATIONS

US Pharmacopeia Compendium of Standards <1216> Tablet Friability, p. 674, 2007.*

(Continued)

*Primary Examiner* — David J Blanchard
*Assistant Examiner* — Alissa Prosser
(74) *Attorney, Agent, or Firm* — Jones Day

(57) ABSTRACT

Disclosed herein are ferric citrate-containing tablets. In various embodiments, the tablets include ferric citrate formulations that meet certain dissolution, tableting and disintegration standards. In various aspects, the tablet formulations can include ferric citrate as the active ingredient and a binder. The formulations also can include a lubricant and/or a disintegrant (which, in some embodiments, can be the same as the binder).

17 Claims, 10 Drawing Sheets

(56) References Cited

U.S. PATENT DOCUMENTS

| | | |
|---|---|---|
| 2011/0060041 A1 | 3/2011 | Hsu et al. |
| 2012/0114747 A1 | 5/2012 | Chan et al. |
| 2012/0115945 A1 | 5/2012 | Le |
| 2012/0121703 A1 | 5/2012 | Fukushima et al. |
| 2012/0238622 A1 | 9/2012 | Ando et al. |
| 2012/0288531 A1 | 11/2012 | Tuvia et al. |
| 2013/0052261 A1 | 2/2013 | Chan et al. |
| 2013/0079537 A1 | 3/2013 | Kwok et al. |
| 2013/0274328 A1 | 10/2013 | Le |
| 2013/0345303 A1 | 12/2013 | Poradosu et al. |
| 2013/0345460 A1 | 12/2013 | Kwok et al. |
| 2014/0011872 A1 | 1/2014 | Kwok et al. |
| 2014/0018420 A1 | 1/2014 | Kwok et al. |
| 2014/0234416 A1 | 8/2014 | Poradosu et al. |
| 2014/0356429 A1 | 12/2014 | Fukushima et al. |
| 2015/0025138 A1 | 1/2015 | Ando et al. |
| 2015/0079168 A1 | 3/2015 | Poradosu et al. |
| 2016/0256486 A1 | 9/2016 | Poradosu et al. |
| 2018/0133191 A1 | 5/2018 | Chan et al. |
| 2018/0214480 A1 | 8/2018 | Chan et al. |
| 2018/0235923 A1 | 8/2018 | Chan et al. |

FOREIGN PATENT DOCUMENTS

| | | |
|---|---|---|
| CA | 2640763 | 7/2008 |
| CA | 2640974 | 7/2008 |
| CN | 1315174 | 10/2001 |
| CN | 03157490.4 | 9/2003 |
| CN | 1446790 A | 10/2003 |
| CN | 03104908.7 | 10/2003 |
| CN | 1600302 | 3/2005 |
| CN | 1751056 A | 3/2006 |
| CN | 101019848 A | 8/2007 |
| CN | ZL 2004800004726.7 | 5/2008 |
| CN | 101235186 A | 8/2008 |
| CN | 101253186 | 8/2008 |
| CN | 101374416 A | 2/2009 |
| CN | 101378658 A | 3/2009 |
| DE | 1131360 | 6/1962 |
| EA | 200501322/26 | 9/2005 |
| EA | 200800593/26 | 3/2008 |
| EA | 010028 | 6/2008 |
| EP | 0308362 | 3/1989 |
| EP | 0600347 | 6/1994 |
| EP | 0868125 | 6/1997 |
| EP | 0959878 | 12/1999 |
| EP | 1601680 | 12/2005 |
| EP | 1704871 A1 | 9/2006 |
| EP | 1931689 | 6/2008 |
| EP | 0959878 | 7/2008 |
| EP | 1978807 | 10/2008 |
| EP | 1978808 | 10/2008 |
| EP | 2360139 A2 | 8/2011 |
| EP | 2594277 | 5/2013 |
| EP | 2594551 A1 | 5/2013 |
| GB | 1224589 | 3/1971 |
| GB | 1226394 | 3/1971 |
| GB | 2212396 A | 7/1989 |
| GB | 2223405 | 4/1990 |
| HK | 1077580 A | 2/2006 |
| ID | W00200502228 | 8/2005 |
| IL | 170382 | 8/2005 |
| IL | 130041/2 | 12/2005 |
| IL | 189583 | 2/2008 |
| IL | 193099 | 7/2008 |
| IL | 192545 | 8/2008 |
| IL | 170382 | 2/2011 |
| IN | 0944/MUMNP/2005 | 8/2005 |
| IN | 393/MUMNP/2008 A | 3/2008 |
| IN | 1414/MUMNP/2008 | 7/2008 |
| IN | 14143/MUMNP/2008 | 7/2008 |
| IN | 244119 | 11/2010 |
| JP | 8198760 A | 8/1996 |
| JP | 2007-133978 | 11/1997 |
| JP | 2001-506262 | 5/2001 |
| JP | 2006-518391 | 8/2006 |
| JP | 2008-552431 | 7/2008 |
| JP | 2008-552435 | 7/2008 |
| JP | 4173553 B2 | 10/2008 |
| JP | 2009-24341 | 2/2009 |
| JP | 2009-504777 | 2/2009 |
| JP | 2009-525276 | 7/2009 |
| JP | 4964585 B2 | 4/2012 |
| KR | 10-0464504 | 12/2004 |
| KR | 10-2005-0107428 | 11/2005 |
| KR | 10-2008-70106131 | 4/2008 |
| KR | 2008-0037083 | 4/2008 |
| KR | 10-2008-0094013 | 10/2008 |
| KR | 10-2008-0106506 | 12/2008 |
| LK | 13792 | 8/2005 |
| MX | 207250 | 3/2002 |
| MX | PA05008784 A | 5/2006 |
| MX | 291484 | 10/2011 |
| MY | PI 2006-3971 | 8/2006 |
| NO | 19992936 | 8/1999 |
| NO | 327148 | 5/2009 |
| NZ | 336060 | 6/1999 |
| NZ | 541991 | 2/2004 |
| NZ | 566743 | 3/2008 |
| NZ | 541991 | 2/2009 |
| NZ | 566743 | 11/2010 |
| PG | PG/P/05/00029 | 8/2005 |
| PG | 000037 | 11/2010 |
| PH | 1-2005-501521 | 8/2005 |
| PL | 69800 | 1/1974 |
| RU | 142643 | 3/1991 |
| RU | 6413558 | 7/2002 |
| RU | 2188033 | 8/2002 |
| RU | 6495177 | 12/2002 |
| RU | 010028 | 6/2008 |
| RU | 20080145410 | 6/2008 |
| SG | 200505259-2 | 8/2005 |
| SG | 114272 | 8/2007 |
| SU | 142643 | 3/1991 |
| TL | 061003938 | 8/2006 |
| TW | 86104116 | 3/1997 |
| TW | 93103743 | 2/2004 |
| TW | 259772 B | 8/2006 |
| TW | 95130373 | 8/2006 |
| VN | 1-2005-01292 | 9/2005 |
| WO | WO 2016/141124 | 9/1916 |
| WO | WO 1990/009102 | 8/1990 |
| WO | WO 97/22266 | 6/1997 |
| WO | WO 1998/026776 | 6/1998 |
| WO | WO 1999/038544 A2 | 8/1999 |
| WO | WO 2004/037048 A1 | 5/2004 |
| WO | WO 2004/074444 | 9/2004 |
| WO | WO 2005/002228 A1 | 1/2005 |
| WO | WO 2007/022435 A2 | 2/2007 |
| WO | WO 2007/088343 | 8/2007 |
| WO | WO 2007/089571 A2 | 8/2007 |
| WO | WO 2007/089577 A2 | 8/2007 |
| WO | WO 2009/062993 | 5/2009 |
| WO | WO 2011/011541 | 1/2011 |
| WO | WO 2012/005340 | 1/2012 |
| WO | WO 2012/006473 A1 | 1/2012 |
| WO | WO 2012/011541 A1 | 1/2012 |
| WO | WO 2013/192565 | 12/2013 |
| WO | WO 2015/066593 | 5/2015 |

OTHER PUBLICATIONS

Almaden, et al., "High Phosphorous Directly Stimulates PTH Secretion by Human Parathyroid Tissue", Journal of the American Society of Nephrology, 1995, vol. 6: 957.

Anjyo, et al., "Medication Advice for Patients with Hypoferric Anemia", Yakkyoku, 1944, vol. 45(5): 55-59. (w/ English Abstract).

Barer et al., "The Effect of Iron on Phosphorous, Calcium, and Nitrogen Metabolism", Journal of Laboratory & Clinical Medicine, 1940, vol. 26: 351-360.

(56) References Cited

OTHER PUBLICATIONS

Block et al., "Re-Evaluation of Risks Associated with Hyperphosphatemia and Hyperparathyroidism in Dialysis Patients: Recommendations for a Change in Management", American Journal of Kidney Diseases, Jun. 2000, vol. 35(6):1226-1237.
Brock, et al., "Rickets in Rats by Iron Feeding", Journal of Pediatrics, 1934, vol. 4:442-453.
Chertow, et al., "Sevelamer attenuates the progression of coronary and aortic calcification in hemodialysis patients", Kidney International, 2002, vol. 62: 245-252.
Chueshov, V. I. et al., "Industrial Technology of Drugs", A Textbook for University Students, Harkov, NPAU Publisher Pharmacy, 2002, pp. 344-346 (in Russian with English translation).
Coburn, et al., "Intestinal Absorption of Calcium and the Effect of Renal Insufficiency", Kidney International, 1973, vol. 4: 96-104.
Coburn, et al., "Study of Intestinal Absorption of Calcium in Patients with Renal Failure", Kidney International, 1973, vol. 3: 264-272.
Cox, et al., "The Effects of High Doses of Aluminum and Iron on Phosphorous Metabolism", Journal of Biological Chemistry, 1931,vol. 92: Xi-Xii.
Cozzolino, et al., "Role of Calcium-Phosphate Product and Bone-Associated Proteins on Vascular Calcification in Renal Failure" J AM Soc Nephrol, 2001, 12: 2511-2516.
Cullen, et al., "A 28-Day Toxicity Study of KRX-0502 (Ferric Citrate) in Rats by Dietary Administration, Keryx Biopharmaceuticals, Inc." (abstract only), 2008.
Cullen, et al., "A 28-Day Toxicity Study of KRX-0502 (Ferric Citrate) in Rats by Dietary Administration, Keryx Biopharmaceuticals, Inc." (poster presentation), 2008.
Deobald, et al., "The Effect of Feeding High Amounts of Soluble Iron and Aluminum Salts", American Journal of Physiology, 1935, vol. 111: 118-123.
Editorial [Unknown Author], "Citrate for Calcium Nephrolithiasis," The Lancet, 1986, vol. 330, pp. 955.
Espacenet machine translation of claims for CN 1446790, 2013.
Espacenet machine translation of description for CN 1446790, 2013.
Ghosh, Amit Kumar, "Letters and Replies: Efficacy of Ferric Citrate as a Phosphate-binding Agent in End-stage Renal Failure", Nephrology Dialysis Transplantation, 2002, vol. 17:1354-1355.
Giachelli, "The Emerging Role of Phosphate in Vascular Calcification" Kidney International, 2009, 75(9): 890-897.
Gimenez, et al., "Prevention of Phosphate-induced Progression of Uremia in Rats by 3-phosphocitric Acid", Kidney International, 1982, vol. 22: 36-41.
Goodman et al., "Coronary-Artery Calcification in Young Adults with End-Stage Renal Disease Who are Undergoing Dialysis", The New England Journal of Medicine, 2000, vol. 342:1478-1483.
Gutteridge J.M.C., "Hydroxyl Radical Formation from the Auto-Reduction of a Ferric Citrate Complex", Free Radical Biology and Medicine, 1991, vol. 11(4):401-406.
Haut, et al., "Renal Toxicity of Phosphate in Rats", Kidney International, 1980, vol. 17: 722-731.
Hollis, Bruce W., "Assay of Circulating 1,25-Dihydroxyvitamin D Involving a Novel Single-Cartridge Extraction and Purification Procedure", Clinical Chemistry, 1986, vol. 32: 2060-2063.
Hou, et al., "Calcium and Phosphorous Fluxes During Hemodialysis with Low Calcium Dialysate", American Journal of Kidney Diseases, 1991, vol. 18: 217-224.
Hsu, Chen Hsing, "Are We Mismanaging Calcium and Phosphate Metabolism in Renal Failure?", American Journal of Kidney Diseases, Apr. 1997, vol. 29(4): 641-649.
Hsu, et al., "Renal Phosphate Excretion in Spontaneously Hypertensive and Normotensive Wistar Kyoto rats", Kidney International, 1984, vol. 25: 789-795.
Hsu, et al., "Factors Influencing Calcitriol Metabolism in Renal Failure", Kidney International, 1990, vol. 37: 44-50.
Hsu, et al., "New Phosphate Binding Agents: Ferric Compounds", Journal of the American Society of Nephrology, 1999, vol. 10:1274-1280.
In-Pharma Technologist.com, Jun. 8, 2005, "Pharma-grade ferric citrate patented", Sep. 17, 2008, http://www.in-pharmatechnologist com/Materials-Formulation/Pharma-grade-ferric-citrate-patented.
International Search Report prepared by the International Searching authority dated Nov. 25, 2010, in PCT Application No. PCT/US2010/042788 (3 pages).
Jacobs, A. et al., "Role of gastric secretion in iron absorption," Gut, 1969, 10:226-229.
Japan, "Japan's Specifications and Standard for Food Additives", 1999, vol. 7: D205-208, D376-382, D428-430, D552-554, D936-938, D1030-1032, D1425-1428.
Karlinsky, et al., "Preservation of Renal Function in Experimental Glomerulonephritis", Kidney International, 1980, vol. 17: 293-302.
Kawatetsu Techno Res. KK, "Manufacture of Ferric Ammonia Citrate, for Supplying Iron Ions in Chemical Reaction, Involves Adding Ammonia Gas and/or Aqueous Ammonia to Iron Citrate", WPIDS (abstract only), 2003.
Kilav, et al., "Parathyroid Hormone Gene Expression in Hypophosphatemic Rats", Journal of Clinical Investigation, 1995, vol. 96: 327-333.
King, Earl Judson, "The Biochemistry of Silicic Acid: The Determination of Silica", The Biochemical Journal, 1939, vol. 33(6):944-954.
King, Earl Judson, et al., "The Biochemistry of Silicic Acid: The Solution and Excretion of Silica", The Biochemical Journal, 1938, vol. 32(2):426-433.
Lakshmanan, et al., "Calcium and Phosphorus Intakes, Balances, and Blood Levels of Adults Consuming Self-selected Diets", American Journal of Clinical Nutrition, 1984, vol. 40: 1368-1379.
Lau, et al., "Fluids and Electrolytes", W.B. Saunders Company, Second Edition, Philadelphia, 1990, Ch. 8: 505-595.
Lau, Kai, "Phosphate Excess and Progressive Renal Failure: The Precipitation-Calcification Hypothesis", Kidney International, 1989, vol. 36: 918-937.
Liu, et al., "Studies of Calcium and Phosphorous Metabolism with Special Reference to Pathogenesis and Effects of Dihydrotachysterol (A.T.10) and Iron", Medicine, 1943, vol. 22: 103-161.
London, et al., "Calcification of the Aortic Valve in the Dialyzed Patient", J Am Soc Nephrol, 2000, 11: 778-783.
Lopez-Hilker, et al., "Phosphorous Restriction Reverses Hyperparathyroidism in Uremia Independent of Changes in Calcium and Calcitriol", American Journal of Physiology, 1990, vol. 259: F432-437.
Lumlertgul, et al., "Phosphate Depletion Arrests Progression of Chronic Renal Failure Independent of Protein Intake", Kidney International, 1986, vol. 29: 658-666.
Martis, et al., "Calcium Cabonate as a Phosphate Binder: Is There a Need to Adjust Peritoneal Dialysate Calcium Concentrations for Patients Using CaCO3?", Peritoneal Dialysis International, 1989, vol. 9: 325-328.
Matkovic, et al., "Calcium Balance during Human Growth: Evidence for Threshold Behavior", American Journal of Clinical Nutrition, 1992, vol. 55: 992-996.
Meyer, et al., "Trace Metal-Citric Acid Complexes as Inhibitors of Calcification and Crystal Growth. I. Effects of Fe(III), Cr(III), and Al(III) Complexes on Calcium Phosphate Crystal Growth", J Urol, 1982, vol. 128:6, 1372-1375.
Moe, et al., "Pathophysiology of Vascular Calcification in Chronic Kidney Disease" Circulation Research, Journal of the American Heart Association, 2004, 560-567.
Moore, C.V., Entry for "Iron", in Modern Nutrition in Health and Disease, Michael G. Wohl and Robert S. Goodhart Eds., Published by Lea & Febiger, Philadelphia, 1968, 339-364.
Naveh-Many, et al., "Parathyroid Cell Mitoses in Normal and Chronic Renal Failure Rats: The Effects of Calcium, Phosphate, and Vitamin D", American Society of Nephrology, 1995, vol. 6: 968.
Niecestro, et al., "A Randomized, Double-Blind, Placebo-Controlled, Dose-Ranging Study of the Effects of Ferric Citrate on Serum Phosphorous Levels in Patients with End Stage Renal

(56) References Cited

OTHER PUBLICATIONS

Disease (ESRD)." (PowerPoint Presentation made at Renal Week of the American Society of Nephrology conference on Nov. 18, 2006).
Niecestro, et al., "Ferric Citrate for the Treatment of Hyperphosphatemia in ESRD." (in Abstract book for 2007 World Congress of Nephrology Conference, 2007, pp: 160-161).
Niecestro, et al., "A Phase II, Randomized, Double-Blind, Placebo-Controlled, Dose-Ranging Study of Ferric Citrate (FC) on Serum Phosphorous Levels in ESRD Patients." (Abstract only), 2006.
Niecestro, et al., "Ferric Citrate (Phosphate Binder): Effects on Serum Iron and Other Parameters in ESRD Patients." (Abstract only), 2006.
Niecestro, et al., "A Randomized, Double-Blind, Placebo-Controlled Dose Ranging Study of the Effects of Ferric Citrate on Serum Phosphorus in Patients with End Stage Renal Disease (ESRD)", Article to be published, 2007.
Niecestro, Robert, "Ferric Citrate for the Treatment of Hyperphosphatemia in ESRD" Abstract of article to be filed, 2007.
Piraino, et al., "Calcium Mass Transfer in Peritoneal Dialysis Patients Using 2.5 mEg/1 Calcium Dialysate", Clinical Nephrology, 1992, vol. 37: 48-51.
Portale, et al., "Effect of Dietary Phosphorous on Circulating Concentrations of 1,25-Dihydroxyvitamin D and Immunoreactive Parathyroid Hormone in Children with Moderate Renal Insufficiency", Journal of Clinical Investigation, 1989, vol. 73: 1580-1589.
Princiotto et al., "Absorption of Oral Chelated Iron", Biochemical Medicine, 1970, vol. 3: 289-297.
Ramirez, et al., "The Absorption of Dietary Phosphorus and Calcium in Hemodialysis Patients", Kidney International, 1986, vol. 30: 753-759.
Rehm, et al., "The Effect of Ferric Chloride on the Utilization of Calcium and Phosphorous in the Animal Body", Journal of Nutrition, 1940, vol. 19: 213-222.
Reinhardt, et al., "A Microassay for 1,25-Dihydroxyvitamin D Not Requiring High Performance Liquid Chromatography: Application to Clinical Studies", Journal of Clinical Endocrinology and Metabolism, 1984, vol. 58(1): 91-98.
Rivet, et al., "Cutaneous Calcification in Patients with End-Stage Renal Disease:, Arch. Dermatol., 2006, vol. 142: 900-906.
Sika, et al., "Evaluation of Ferric Citrate as a Phosphate Binder in Dialysis Patients Requiring High Doses of Phosphate Binder", Zerenex Poster presented at the American Society of Nephrology Conference, Oct. 2009.
Slatopolsky, et al., "On the Pathogenesis of Hyperparathyroidism in Chronic Experimental Renal Insufficiency in the Dog", Journal of Clinical Investigations, 1971, vol. 50: 492-499.
Slatopolsky, et al., "Phosphate (PO) Restriction Prevents Parathyroid Cell Growth in Uremic Rats and High Phosphate Directly Stimulates PTH Secretion in Tissue Culture", American Society of Nephrology, 1995, vol. 6: 971.
Spiro, et al., "The Hydrolytic Polymerization of Ferric Citrate. T. The Chemistry of the Polymer", Journal of the American Chemical Society, 1967, vol. 89: 5555-5559.
Terato, et al., "Studies on Intestinal Absorption of Iron. I. Effects of Sugars, Polyalcohols and Organic Acids on Hydrolytic Polymerization of Iron", Journal of the Pharmaceutical Society of Japan, 1972, vol. 92(10):1247-1251.
The Ferric Citrate Study Group, A Phase II Randomised, Double-Blind, Placebo-controlled, Dose-Ranging, Study of Ferric Citrate (FC) on Serum Phosphorous Levels Abstract of Patent application to be filed, 2006.
The Ferric Citrate Study Group, "Effects on Iron Parameters in End-Stage Renal Disease Patients" Abstract of Patent application to be filed, 2006.
The Ferric Citrate Study Group, "A Phase II Ramdomized, Double-Blind, Placebo-Controlled, Dose-Ranging Study of Ferric Citrate (FC) on Serum Phosphorous Levels" Abstract of Patent application to be filed, 2007.

The Ferric Citrate Study Group, "Ferric Citrate: Effects on Iron Parameters, Hematocrit, and Hemoglobin in End-Stage Renal Disease Patients" Abstract of Patent application to be filed, 2007.
The Merck Index, 12$^{th}$ Ed., "Acetic, Citric, Fumaric, Isocitric, succinic and tartaric acid". Published Feb. 1996.
Thomas, W.C., "Trace Metal-Citric Acid Complexes as Inhibitors of Calcification and Crystal Formation", Proc. Soc. Exp. Biol. Med., 1982, vol. 170:3, 321-327.
Tonelli, et al., "Oral Phosphate Binders in Patients with Kidney Failure", New Engl J Med, 2010, 362: 1312-1324.
Webster's II New Riverside University Dictionary, 1984, Riverside Publishing Company, p. 763.
Yamamoto, et al., "Interaction between Various Phosphate Compounds and Iron Compounds Containing Sodium Ferrous Citrate", Shinyaku & Rinsho, 1995, vol. 44(5):9-15. (w/English Abstract).
Yang, et al., "An Open-Label, Crossover Study of a New Phosphate-Binding Agent in Haemodialysis Patients: Ferric Citrate", Nephrology Dialysis Transplantation, 2002, vol. 17:265-270.
Office Action dated Apr. 5, 2013 issued by Russian Patent Office in relation to Russian Patent Application No. 2012106139.
European Pharmacopoeia 6.0, Chapter 2.9.1, "Disintegration of Tablets and Capsules"; 2007.
European Pharmacopoeia 6.0, Chapter 2.9.3, "Dissolution Test for Solid Dosage Forms"; 2007.
Office Action dated Aug. 4, 2014 issued by Russian Patent Office in relation to Russian Patent Application No. 2012106139 (with English Translation).
Office Action dated Aug. 29, 2014 issued by United States Patent and Trademark Office in relation to U.S. Appl. No. 14/262,465.
Singh et al., "Correction of Anemia with Epoetin Alfa in Chronic Kidney Disease", New Engl J Med, 2006, 355:2085-2098.
FLM1 fluid bed dryer granulator: http://www.starind.com/View/Vector-Freund-FL-M-1-6635, printed 2014.
Mattes et al., "In-line process analysis of residual moisture in a fluid bed granulator-dryer using NIR spectroscopy," Spectroscopy, Jan. 2005; http://www.niroinc.com/html/pharma/phpdfs/nir_spectroscopy.pdf.
Office Action dated Apr. 22, 2014 issued by United States Patent and Trademark Office in relation to U.S. Appl. No. 13/913,909.
Office Action dated Feb. 26, 2015 issued by United States Patent and Trademark Office in relation to U.S. Appl. No. 13/913,909.
"A 4-Week dose-ranging and efficacy trial of KRX-0502 (Ferric Citrate) in patients with end-stage renal disease", Clinicaltrials.gov.archive, Jan. 4, 2011, https://clinicaltrials.gov/archive/NCT01074125/2010_06_02.
"Trial of a New Formulation of KRX-0502 (Ferric Citrate) in Patients with End-Stage Renal Disease", Clinical Trials.gov.archive, Jun. 2, 2010, https://clinicaltrials.gov/archive/NCT00967993/2010/2010_06_02.
Agarwal et al., "A Randomized Controlled Trial of Oral versus Intravenous Iron in Chronic Kidney Disease", Am J Nephrol, 2006, 26:445-454.
Akmal et al., "The prevalence and significance of occult blood loss in patients with predialysis advanced chronic renal failure (CRF), or receiving dialytic", Clin Nephrol, 1994, 42:198-202.
Ballot et al., 1987, "The effect of fruit juices and fruits on the absorption of iron from a rice meal", Br J Nutr, 57:331-343.
Bellasi et al. "Phosphate binders: New products and challenges", Hemodialysis International, 2006, 10:255-234.
CPG and CPR 3.2 Using Iron Agents, Am J Kidney Dis, 2006, 47:S58-S70.
CRC Handbook of Chemistry and Physics, 76th Edition, CRC Press, Inc., 1995, David R. Lide, editor-in-chief, pp. 12-1 to 12-6.
Database on CAPLUS, An 1995:828125, "Effect of iron as a new type of phosphate binder in hemodialysis patients", Kuroda et al., J Nephrol, 1995, 78(8): pp. 468-473, abstract only.
Eschbach and Adamson "Iron overload in renal failure patients: changes since the introduction of erythropoietin therapy", Kidney Int., Mar. 1999, vol. 55, No. S69, pp. S35-S43.
Fishbane et al., "Iron Indices in Chronic Kidney Disease in the National Health and Nutritional Examination Survey 1988-2004", Clin J Am Soc Nephrol, 2009, 4:57-61.

(56) References Cited

OTHER PUBLICATIONS

Fishbane et al., "Iron management in end-stage renal disease", Am J Kidney Dis, 1997, 29:319-33.
Gillooly et al., 1983, "The effects of organic acids, phytates and polyphenols on the absorption of iron from vegetables", Br J Nutr, 49:331-342.
Gotloib et al., "Iron deficiency is a common cause of anemia in chronic kidney disease and can often be corrected with intravenous iron", J Nephrol, 2006, 19:161-7.
Hsu et al., "Iron status and hemoglobin level in chronic rena", J Am Soc Nephrol, 2002, 13:2783-6.
Kalantar-Zadeh et al., "Intravenous Iron Versus Erythropoiesis Stimulating Agents: Friends or Foes in Treating Chronic Kidney Disease Anemia?", Adv Chronic Kidney Disease, Mar. 2009, 16(2): 143-151.
Kooistra et al., "Iron absorption in erythropoietin treated haemodialysis patients: Effects of iron availability, inflammation and aluminium", Nephrol Dial Transplant, 1998, 13:82-8.
Kuroda et al., 1995, "Effect of iron as a new type of phosphate binder in hemodialysis patients", Jpn J Nephrol, 37:468-473.
MacDougall, "Iron supplementation in the non-dialysis chronic kidney disease (ND-CKD) patient: oral or intravenous?", Curr Med Res Opin, 2010, 26(2):473-82.
Mafra et al., "Iron and zinc status of patients with chronic renal failure who are not on dialysis", J Ren Nutr, 2002, 12:38-41.
Mathew et al., 2006, "The role of hyperphosphataemia in vascular calcification (VC): Actions of lanthanum carbonate (LaCO3)", J Am Soc Nephrol, 17:357A.
Mehdi et al., "Anemia, Diabetes, and Chronic Kidney Disease", Diabetes Care, Jul. 2009, 32:1320-1326.
Nissenson AR and Strobos J "Iron deficiency in patients with renal failure", Mar. 31, 1999, vol. 55, No. S69, pp. S18-S21.
Post et al., "Iron deficiency in patients with chronic kidney disease: potential role for intravenous iron therapy independent of erythropoietin", Int Urol Nephrol, 2006, 38: 719-23.
Remington Chapter 35 "Dissolution" 2005.
Salovaara et al., 2002, "Organic acids influence iron uptake in the human epithelial cell line Caco-2", J Agric Food Chem, 50:6233-6238.
Sika et al., 2010, "Prolonged Use of Ferric Citrate (FC) as a Phosphate Binder Reduces IV Iron Use in Pts with ESRD", J Am Soc Nephrol, 21:2010, pp. 783A-784A, Abstract SA-PO2946.
Spinowitz et al., 2008, "Ferumoxytol for Treating Iron Deficiency Anemia in CKD", J Am Soc Nephrol, 19:1599-605.
Tagboto et al., 2009, "The Efficacy of a Single Dose of Intravenous Ferric Carboxymaltose (Ferinject®) on Anemia in a Pre-dialysis Population of Chronic Kidney Disease Patients", J Ren Care, 35(1):18-22.
The United States Pharmacopeia USP 26 NF 21, <1216>, "Tablet Friability"; 2003.
Tonelli et al., 2005, "Relation between serum phosphate level and cardiovascular event rate in people with coronary disease" Circulation, 112:2627-2633.
US Pharmacopeia: "USP 701 Dissolution Test Method", Aug. 1, 2008. Retrieved from the internet: Url:http://www.usp.org/sites/default/files/usp_pdf/EN/USPNF/generalChapter701.pdf.
Voormolen et al., 2007, "High plasma phosphate as a risk factor for decline in renal function and mortality in pre-dialysis patients", Nephrol Dial Transplant, 22:2909-2916.
Zhang et al., 2007, "Improved iron bioavailability in an oat-based beverage: the combined effect of citric acid addition, dephytinization and iron supplementation", Eur J Nutr, 46:95-102.
American Chemical Society, "Ferric Citrate", Chemical Abstracts, 1961, vol. 55 (3): 3939d.
Ang and Lang, 2008, "The prognostic value of the ECG in hypertension: where are we now?", J Hum Hypertens; 22:460.
Arogundade et al., 2013, "Iron status and benefit of the use of parental iron therapy in pre-dialysis Chronic Kidney Disease patients", Nigerian Postgraduate Medical Journal, vol. 20, No. 4: 299-304.

Barrios et al., 2008, "Prevalence of left ventricular hypertrophy detected by Cornell voltage-duration product in a hypertensive population", Blood Press.; 17:110.
Beache et al., 2001, "Attenuated myocardial vasodilator response in patients with hypertensive hypertrophy revealed by oxygenation-dependent magnetic resonance imaging", Circulation; 104:1214.
Block, et al., 2012, "Effects of Phosphate Binders in Moderate CKD", J. of Am. Soc. Nephrology, 23: 1407-1415.
Carluccio et al., 2000, "Prognostic value of left ventricular hypertrophy and geometry in patients with a first, uncomplicated myocardial infarction", Int J Cardiol; 74:177.
Clarkson, et al., "The Effect of a High Intake of Calcium Carbonate in Normal Subjects and Patients with Chronic Renal Failure", Clinical Science, 1966, vol. 30: 425-438.
Elias et al., 2007, "Left ventricular mass, blood pressure, and lowered cognitive performance in the Framingham offspring", Hypertension, 49:439.
FLM1 fluid bed dryer granulator: http://blog.fedequip.com/post/2013/06/25/Vector-Fluid-Bed-Dryer-Granulator-Model-FLM1.aspx, dated Jun. 25, 2013.
Faul et al., 2011, "FGF23 induces left ventricular hypertrophy", J Clin Invest;121(11):4393-4408.
Ganz and Nemeth, 2016, "Iron Balance and the Role of Hepcidin in Chronic Kidney Disease", Semin Nephrol, 36:87-93.
Koren et al., 1991, "Relation of left ventricular mass and geometry to morbidity and mortality in uncomplicated essential hypertension", Ann Intern Med; 114:345.
Levy et al., 1990, "Prognostic implications of echocardiographically determined left ventricular mass in the Framingham Heart Study", N Engl J Med; 322:1561.
Locatelli et al., 2016, "Iron Therapy Challenges for the Treatment of Nondialysis CKD Patients", Clin. J. Am. Soc. Nephrol., 11: 1269-1280.
McClellan et al., 2004, "The prevalence of anemia in patients with chronic kidney disease", Curr Med Res Opin, 20 (9):1501-1510.
Pierdomenico et al., 2008, "Regression of echocardiographic left ventricular hypertrophy after 2 years of therapy reduces cardiovascular risk in patients with essential hypertension", Am J Hypertens; 21:464.
Quinibi, 2010, "The efficacy and safety of current intravenous iron preparations for the management of iron-deficiency anaemia: a review", Arzneimittel Forschung Drug Research, 60:399-412.
US Pharmacopeia: "USP 711 Dissolution Test Method", Dec. 1, 2011. Retrieved from the internet: URL:http://www.usp.org/sites/default/files/usp_pdf/EN/USPNF/2011-02-25711DISSOLUTION.pdf.
Verdecchia et al., 2001, "Left ventricular mass and cardiovascular morbidity in essential hypertension: the MAVI study", J Am Coll Cardiol; 38:1829.
Li et al., 2003, "PUB324: The effects of oral vs venous iron supplement in treatment of iron deficiency of maintained patients with anemia", J. of Amer. Society of Nephrol; Meeting of The Amer. Society of Nephrol. Renal Week, Williams and Wilkins, Baltimore, MD, US; San Diego, CA, USA, vol. 14, abstract issue: 842A-843A.
Remington, 1985, Remington's Pharmaceutical Sciences, Mack Publishing Company: 1603-1608.
Albaaj et al., "Hyperphosphataemia in Renal Failure: Causes, Consequences and Current Management," Drugs 63(6):577-596 (2003).
Amin, "The impact of improved phosphorus control: use of sevelamer hydrochloride in patients with chronic renal failure," *Nephrol. Dial. Transplant.*, 17:340-345 (2002).
Apelblat, "Solubilities of Organic Salts of Magnesium, Calcium, and Iron in Water", *J. Chem. Thermodynamics*, 25:1443-1445 (1993).
Belloni, "Organic Iron Salts," *Italian Chemistry Journal*, 159-212 (1920).
Berge et al., "Pharmaceutical Salts," *J. Pharm. Sci.*, 66(1):1-19 (1977).
Bernacca et al., "Chemical modification of bovine pericardium and its effect on calcification in the rat subdermal model." *Biomaterials*, 13(6):345-352 (1992).

(56) References Cited

OTHER PUBLICATIONS

Bhatia et al., "Corneo-conjunctival changes in chronic renal failure," *Kobe J. Med. Sci.*, 32(4):133-140 (1986).
Bindroo et al., *Renal Failure*, StatPearls Publishing LLC, Treasure Island, Florida, 1-8 (2018).
Block et al., "A 12-week, double-blind, placebo-controlled trial of ferric citrate for the treatment of iron deficiency anemia and reduction of serum phosphate in patients with CKD stages 3-5," *Am. J. Kidn.*, 65(5):728-736 (2015).
Block et al., "Association of serum phosphorus and calcium x phosphate product with mortality risk in chronic hemodialysis patients: a national study," *Am. J. Kidney Dis.*, 31(4):607-617 (1998).
Block, et al., "Phosphate Homeostasis in CKD: Report of a Scientific Symposium Sponsored by the National Kidney Foundation," *Am. J. Kidney Dis.*, 62:457-473 (2013).
Boclair et al., "Layered Double Hydroxide Stability. 1. Relative Stabilities of Layered Double Hydroxides and Their Simple Counterparts," *Chem. Materials*, 11:298-302 (1999).
Bolasco, "Effects of the Use of Non-Calcium Phosphate Binders in the Control and Outcome of Vascular Calcifications: A Review of Clinical Trials on CKD Patients," Int. J. Nephrol., 2011:758450 (2011).
Bond et al., "A meta-analysis of ferric citrate for hyperphosphatemia: The effect of an oral iron-containing phosphate binder on serum ferritin and and saturated transferrin in hemodialysis patients," *Nephrology Dialysis Transplantation*, 27(Supp. 2): ii490 (2012).
Bond et al., "Ferric citrate: an iron-based oral phosphate binder," *Kidney Res. Clin. Pract.*, 31(20):A38, Abstract 90 (2012).
Chan et al., "Nocturnal haemodialysis is associated with improved vascular smooth muscle cell biology," *Nephrol. Dial. Transplant.*, 24:3867-3871 (2009).
Chaumeil, "Micronization: a method of improving the bioavailability of poorly soluble drugs," *Methods Find Ex. Clin. Pharmacol.*, 20(3):211-215 (1998).
Field et al., "Composition and Stability of Iron and Copper Citrate Complexes in Aqueous Solution," *Can. J. Chem.*, 52:3119-3124 (1974).
Furugouri, "Effect of elevated dietary levels of iron on iron store in liver, some blood constituents and phosphorus deficiency in young swine," *J. Animal Sci.*, 34(4):573-577 (1972).
Ganesh et al., "Association of Elevated Serum $PO_4$, Ca X $PO_4$ Product, and Parathyroid Hormone with Cardiac Mortality Risk in Chronic Hemodialysis Patients,"*J. Am. Soc. Nephrol.*, 12:2131-2138 (2001).
Hegsted et al., "The Influence of Diet on Iron Absorption," *J. Exp. Med.*, 90(2):137-146 (1949).
Highlights of Prescribing Information for Auryxia, Datasheet [online] Nov. 2014 [Retrieved on Apr. 19, 2016]. Retrieved from the Internet: URL:https://auryxia.com/wp-content/uploads/Auryxia_PI_Keryx_112014.pdf.
Keryx Press Release, "Keryx Biopharmaceuticals Announces Positive Top-Line Results From Pivotal Phase 3 Study of Ferric Citrate For the Treatment of Iron Deficiency Anemia in Adults with Non-Dialysis Dependent Chronic Kidney Disease," Mar. 29, 2016.
Keryx Press Release, "Keryx Biopharmaceuticals Announces Zerenex(TM) (ferric citrate coordination complex) Meets All Primary and Key Secondary Endpoints in Phase 2 Study of Non-Dialysis Dependent Chronic Kidney Disease Patients With Elevated Serum Phosphorus and Iron Deficiency Anemia," Nov. 5, 2013.
Keryx Press Release, "Keryx Biopharmaceuticals Announces Zerenex(TM) (Ferric Citrate Coordination Complex) Phase 2 Results in Non-Dialysis Dependent Chronic Kidney Disease Selected as a Late Breaking Oral Presentation at the Upcoming National Kidney Foundation 2014 Spring Clinical Meeting," Apr. 9, 2014.
Kesisoglou et al., "Nanosizing—Oral Formulation Development and Biopharmaceutical Evaluation," *Adv. Drug Deliv. Rev.*, 59:631-644 (2007).

Kidney Disease Improving Global Outcomes (KDIGO) Anemia Work Group, KDIGO Clinical Practice Guideline for Anemia in Chronic Kidney Disease, "Chapter 2: Use of iron to treat anemia in CKD," *Kidney Inter. Suppl.*, 2(4):292-298 (2012).
King et al., " Chapter 90: Oral Solid Dosage Forms," *Remington's Pharmaceutical Sciences, 17 th Edition*, Mack Printing Company, Easton Pennsylvania, 1603-1632 (1985).
Laflamme et al., "Bone and Soft Tissue Changes with Oral Phosphate Supplements," *J. Clin. Inv.*, 51:2834-2840 (1972).
Lewis et al., "Ferric citrate controls phosphorus and delivers iron in patient on dialysis," *J. Am. Soc. Nephrol.*, 26:493-503 (2015).
Lida et al., "Ferric citrate hydrate, a new phosphate binder, prevents the complications of secondary hyperparathyroidism and vascular calcification," *Am. J. Nephrol.*, 37:346-358 (2013).
Massry et al., "Vascular calcification and peripheral necrosis in a renal transplant recipient. Reversal of lesions following subtotal parathyroidectomy," *Am. J. Med.*, 49(3):416-422 (1970).
Mutell et al., "Reduced Use of Erythropoiesis-Stimulating Agents and Intravenous Iron with Ferric Citrate: A Medicare Bundle Cost-Offset Model," 6/2, vol. 15, No. 4, p. A155, Abstract No. PUK16 (2012).
National Kidney Foundation, 2014, "Clinical Update: CKD-MBD and Anemia—Benefits and Risks associated with Common Therapies" (A study supported by an unrestricted grant from Keryx).
National Kidney Foundation, KDOQI Clinical Practice Guidelines for Chronic Kidney Disease: Evaluation, Classification and Stratification, *Am. J. Kidney Disease*, 29, S1-S266 (2002).
Oren et al., "Calcium oxalate kidney stones in patients on continuous ambulatory peritoneal dialysis," *Kidney Int.*, 25:534-538 (1984).
Quinbi et al., "A randomized controlled trial comparing intravenous ferric carboxymaltose with oral iron for treatment of iron deficiency anaemia of non-dialysis-dependent chronic kidney disease patients," *Nephrol. Dial. Transplant.*, 26:1599-1607 (2011).
Ritz et al., "Compounds in development to combat hyperphosphataemia," *Expert Opin. Investig. Drugs*, 10(12):2185-2190 (2001).
Rowe et al., "Magnesium Stearate," *Handbook of pharmaceutical Excipients, Fifth Edition*, 430-433 (2006).
Rowe et al., "Starch," *Handbook of pharmaceutical Excipients, Fifth Edition*, 725-730 (2006).
Santiago, "Ferrous versus ferric oral iron formulations for the treatment of iron deficiency: a clinical overview," *Scientific World Journal*, Article ID 846824 (2012).
Sekercioglu et al., "Comparative Effectivenes of Phosphate Binders in Patients with Chronic Kidney Disease: A Systematic Review and Network Meta-Analysis," *PLoS ONE* 11(6): e0156891 (2016).
Sheikh et al., "Reduction of dietary phosphorus absorption by phosphorus binders. A theoretical, in vitro, and in vivo study," *J. Clin. Invest.*, 83:66-73 (1989).
Sika et al., "A dose-ranging and efficacy phase 3 trial of ferric citrate (FC) as a phosphate binder in dialysis patients," *Am. J. Kidney Disease*, 57(4): A89 (2011).
Suzuki et al., "Iron chelated cyclic peptide, ferrichrysin, for oral treatment of iron deficiency: solution properties and efficacy in anemic rats," *Int. J. Vitam. Nutr. Res.*, 77(1):13-21 (2007).
*The Merck Index*, 8th Edition., "ferric citrate," Merck & Company, p. 452 (1968).
Tensova A.I., *Dosage form and therapeutic efficiency of drugs: Introduction to biopharmacy*, pp. 47-48 (1974).
Timberlake, "Iron-Malate and Iron-Citrate Complexes," *J. Chem. Soc.*, 5078-5085 (1964).
Tokuyama et al., "Conjunctival and Corneal Calcification and Bone Metabolism in Hemodialysis Patients," *Am. J. Kidney Dis.*, 39(2):291-296 (2002).
Umanath et al. "Rationale and study design of a three-period, 58-week trial of ferric citrate as a phosphate binder in patients with ESDR on dialysis," *Hemodialysis International*, 17:67-74 (2013).
Umanath et al., "Ferric citrate reduces intravenous iron and erythropoiesis-stimulating agent use in ESRD," *J. Am. Soc. Nephrol.*, 26:2578-2587 (2015).

(56) References Cited

OTHER PUBLICATIONS

United States Department of Health and Human Services, *Guidance for Industry: Q3B(R2) Impurities in New Drug Products*, Food and Drug Administration, Rockville, MD, Jul. 2006.

United States Pharmacopeia, "Apparent Intrinsic Dissolution—Dissolution Testing Procedures for Rotating Disk and Stationary Disk," 37-NF 32, Section 1087, 831-834 (2014).

United States Pharmacopeia, "Intrinsic Dissolution," 24-NF 19, Section 1087, 2706-2707 (1999).

United States Pharmacopeia, "Intrinsic Dissolution," 25-NF 20, Section 1087, 2159-2160 (2002).

United States Pharmacopeia, "Specific Surface Area," 29-NF 24, Section 846, 2767-2769 (2006).

Viegas et al., "Measurement of Intrinsic Drug Dissolution Rates Using Two Types of Apparatus," *Pharm. Tech.*, 44-53 (2001).

Vo et al., "Are there ways to attenuate arterial calcification and improve cardiovascular outcomes in chronic kidney disease?," *World. J. Cardiol.*, 6(5):216-226 (2014).

Wadke et al., *Pharmaceutical Dosage Forms: Tablets, vol. 1*, "Preformulation Testing IV. Particle Size, Shape and Surface Area," Marcel Decker Inc., New York, NY, Chapter 1 (1980).

Warner et al., "The Cupric and Ferric Citrate Complexes," *J. Am. Chem. Soc.*, 75:5086-5094 (1953).

Weber et al., "Effect of dietary fibre mixture on growth and intestinal iron absorption in rats recovering from iron-deficiency anaemia," *British J. Nutrition*, 104(10):1471-1476 (2010).

Wojcicki, "Hyperphosphatemia is associated with anemia in adults without chronic kidney disease: results from the National Health and Nutrition Examination Survey(NHANES): 2005-2010," *BMC Nephrol.*, 14:178 (2013).

Yokoyama et al., "Effect of oral JTT-751 (ferric citrate) on hyperphosphatemia in hemodialsysi patients: results of a randomized, double-blind, placebo-controlled trial," *Amer. J. Nephphrol.*, 36(5):478-487 (2012).

Yokoyama et al., "Ferric Citrate Hydrate for the Treatment of Hyperphosphatemia in Nondialysis-Dependent CKD," *Clin. J. Am. Soc. Nephrol.*, 9:543-552 (2014).

\* cited by examiner

FERRIC CITRATE DOSAGE FORMS

CROSS REFERENCE TO RELATED APPLICATIONS

This application is a divisional of U.S. patent application Ser. No. 13/255,326, filed Sep. 8, 2011, which is a national stage of International Patent Application No. PCT/US2010/042788, filed Jul. 21, 2010, which claims priority to U.S. Provisional Patent Application No. 61/227,124, filed Jul. 21, 2009, each of which is hereby incorporated by reference herein for all purposes in their entirety.

FIELD

The field of the disclosure generally relates to pharmaceutical compositions of ferric citrate, methods for their use in treating medical conditions, and processes for their manufacture.

BACKGROUND

U.S. Pat. No. 5,753,706 discloses that ferric citrate compounds can be used to control phosphate metabolism and prevent metabolic acidosis in patients. The contents of U.S. Pat. No. 5,753,706 are incorporated herein in its entirety by reference. Ferric citrate compounds can be used with patients suffering from renal failure associated with hyperphosphatemia or patients predisposed to development of a hyperphosphatemic condition. Ferric citrate also is used as a food supplement and additive. Ferric citrate is characterized as a light brown to beige powder, odorless and slightly ferruginous tasting. According to the Merck Index, ferric citrate is slowly but completely soluble in cold water and readily soluble in hot water but diminishes in solubility with age.

U.S. Pat. No. 6,903,235 discloses that ferric citrate is commercially available in the form of a combination of iron and citric acid of indefinite composition. The contents of U.S. Pat. No. 6,903,235 are incorporated herein in its entirety by reference. The '235 Patent explains that the indefinite composition is likely due to difficulties encountered in its preparation but that those knowledgeable in the art understand and necessarily accept that commercially available ferric citrate contains different molar ratios of iron and citric acid and also contains different amounts of water.

WO 2004/074444 discloses processes for making ferric organic compounds, such as ferric citrate, with enhanced dissolution rates. WO 2007/022435 is a continuation-in-part of WO 2004/074444 and discloses processes for making ferric organic compounds soluble over a wide pH range and having a large surface area. WO 2007/089577 is directed to methods of treating soft tissue calcification using ferric organic compounds, such as a ferric citrate compound. WO 2007/089571 is directed to methods of treating chronic kidney disease using ferric organic compounds, such as ferric citrate compounds.

SUMMARY

In one aspect, the disclosure is directed to a tablet including ferric citrate. In some embodiments, the tablet can include at least 65 weight percent ferric citrate.

In another aspect, the disclosure is directed to a tablet comprising granule particles. The granule particles include ferric citrate and a binder, and the mean surface area to mass ratio of the granule particles is equal to or greater than 1 $m^2$ per gram. In various embodiments, the mean surface area to mass ratio of said granule particles is equal to or greater than 5 $m^2$ per gram or 10 $m^2$ per gram.

In another aspect, the tablet can include at least 70 weight percent ferric citrate, at least 80 weight percent ferric citrate, or at least 90 weight percent ferric citrate.

In another aspect, the binder can be one or more of hydroxypropyl cellulose (HPC), hydroxypropylmethyl cellulose (HPMC), sodium alginate, alginic acid, guar gum, acacia gum, xanthan gum, carbolpol, cellulose gum (carboxymethyl cellulose), ethyl cellulose, maltodextrin, PVP/VA, povidone, microcrystalline cellulose, starch (partially or fully pregelatinized starch) and methyl cellulose.

In another aspect, the tablet can include various additional components including, for example, one or more disintegrants and/or one or more lubricants. The disintegrant can be one or more of microcrystalline cellulose, croscarmellose sodium, crospovidone, sodium starch glycolate, and starch. The lubricant can be one or more of magnesium stearate, calcium stearate, sodium stearyl fumarate, polyethylene glycol (molecular weight above 3350), sodium lauryl sulfate, talc, mineral oil, leucine, and poloxamer. In some embodiments, the tablet can include between approximately 65% and 92% ferric citrate, between approximately 4.5% and 30% binder, and between 0.5% and 3% lubricant. The binder can have disintegrant properties. The binder can be pregelatinized starch.

In another aspect, the tablet can be between approximately 65% and 92% ferric citrate, between approximately 4.5% and 30% binder, between approximately 1.5% and 15% disintegrant, and between 0.5% and 3% lubricant.

Various additional components in the tablet can include microcrystalline cellulose, pregelatinized starch and sodium stearyl fumarate. In one embodiment, the ferric citrate can be present at approximately 85 weight percent, the microcrystalline cellulose present at approximately 4 weight percent, the pregelatinized starch present at approximately 9 weight percent, and the sodium stearyl fumarate present at approximately 2 weight percent.

In another aspect, the tablet can have between approximately 10% and 60% of ferric citrate dissolved in about 15 minutes, between approximately 30% and 90% of ferric citrate dissolved in about 30 minutes and at least approximately 60% of the ferric citrate dissolved in about 60 minutes in a dissolution test according to test method USP <711>. The tablet can have a dissolution of at least 90% within 30 minutes in a dissolution test according to test method USP <711>. The tablet can show a dissolution of at least 90% within 60 minutes in a dissolution test according to test method USP <711>.

The tablet can show a disintegration time of less than 30 minutes in a disintegration test according to test method USP <701>. The tablet can show a disintegration time of greater than 30 minutes in a disintegration test according to test method USP <701>.

The tablet can include approximately 1000 mg of ferric citrate, approximately 667 mg of ferric citrate, approximately 500 mg of ferric citrate, approximately 250 mg of ferric citrate, or approximately 125 mg of ferric citrate.

In various aspects, the LOD (loss on drying) % water in the tablet is less than 20% water w/w. In other aspects, the LOD % water of the tablet is less than 15% water w/w. In still other aspects, the LOD % water of the tablet is less than 10% water w/w.

In various aspects, at least 80% of the ferric citrate in the tablet is dissolved in a time less than or equal to 60 minutes as measured by test method USP <711>.

In another aspect, the tablet includes a disintegrant. In certain embodiments, the disintegrant can be selected from one or more of microcrystalline cellulose, croscarmellose sodium, crospovidone, sodium starch glycolate, and starch.

In another aspect, the tablet includes a lubricant. In certain embodiments, the lubricant can be selected from one or more of magnesium stearate, calcium stearate, and sodium stearyl fumarate.

In another aspect, the disclosure is directed to a method of preparing a ferric citrate tablet. The method includes mixing the ferric citrate with one or more binders under conditions in which the LOD % water does not exceed 25% to form ferric citrate granules. Granulation can be performed by any method known in the art (e.g., fluid bed granulation or high shear granulation). The ferric citrate granules are then tableted.

In another aspect, the tablets are heated to above 50° C. after tableting.

The tablets can be used for the prophylaxis or treatment of a variety of diseases or disease states, including, but not limited to, hyperphosphatemia.

Embodiments of the method can include one or more of the features described above or herein.

The details of various embodiments are set forth in the accompanying drawings and the description below. Features and advantages of various embodiments are apparent from the description, the drawings, and the claims.

DESCRIPTION OF THE DRAWINGS

Those skilled in the art will understand that the drawings, described herein, are for illustration purposes only. The drawings are not intended to limit the scope of the present disclosure.

DETAILED DESCRIPTION

Figure 1:
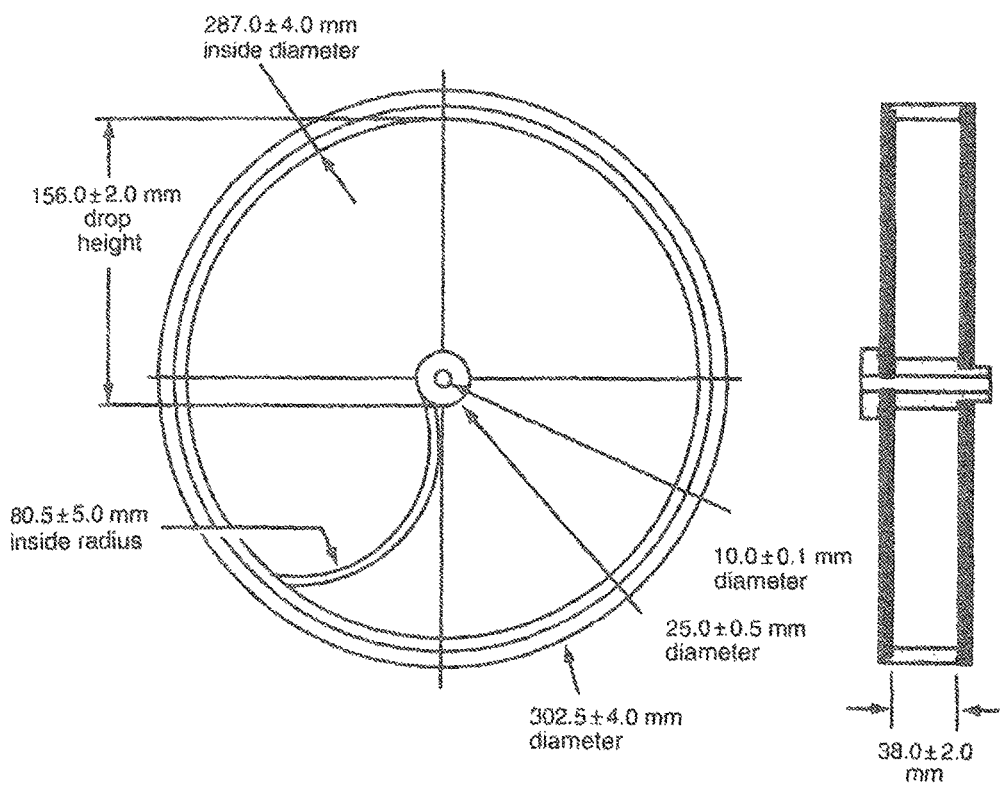
FIG. 1 depicts a Tablet Friability Apparatus.

Disclosed herein are ferric citrate-containing tablets. In various embodiments, the tablets include ferric citrate formulations that meet certain dissolution, tableting and disintegration standards. In various aspects, the tablet formulations can include ferric citrate as the active ingredient and a binder. The formulations also can include a lubricant and/or a disintegrant (which, in some embodiments, can be the same as the binder).

Tablets

In one aspect, the formulation is a tablet that includes ferric citrate and a binder. As is used herein, a "tablet" is a material produced by compression force, such as with a tableting machine. In other embodiments the formulation or tablet can include ferric citrate, a binder, a lubricant and a disintegrant. The tablet or formulation can be used as a prophylaxis or treatment for hyperphosphatemia by administering the tablet or formulation in an effective amount or amounts known in the art.

The formulation can be characterized as highly drug loaded with the ferric citrate present in the formulation at values of greater than approximately 65% by weight of the formulation, greater than approximately 70% by weight of the formulation and as high as approximately 92% of the formulation. Intermediate values such as approximately 80% by weight ferric citrate, approximately 85% by weight ferric citrate and approximately 90% by weight ferric citrate also can be used in the ferric citrate formulation. The characteristics of the tablet produced at these highly loaded weight percentages are controlled by variables such as binder, binder amount, disintegrant, disintegrant amount, formulation method used (e.g., granulation, direct compression), tableting parameters, etc. Thus if a tablet is made and it has a slight amount of lamination or capping, by varying one or more of the above variables the lamination or capping can be corrected.

In various embodiments, the tablet formulation contains one or more components selected from among one or more binders, one or more lubricants, and one or more disintegrants.

The binder can be any binder known in the art. Without limitation, examples of the binder can include one or more of hydroxypropyl cellulose (HPC), hydroxypropylmethyl cellulose (HPMC), sodium alginate, alginic acid, guar gum, acacia gum, xanthan gum, carbolpol, cellulose gum (carboxy methyl cellulose), ethyl cellulose, maltodextrin, PVP/VA, povidone, microcrystalline cellulose, starch (partially or fully pregelatinized starch) and methyl cellulose. The maltodextrin, PVP/VA, and methyl cellulose function as immediate release binders when used in the ferric citrate formulations.

It also should be understood that combinations of binders can be used to control and vary the effect of the binder. For example, a binder system can be made up of hydroxypropyl cellulose and polyvinyl pyrrolidone (povidone) with or without microcrystalline cellulose. One or both of the hydroxypropyl cellulose and povidone can be replaced with pregelatinized starch.

In various aspects, the tablet can include a lubricant. As an example of a lubricant for the ferric citrate formulations, magnesium stearate, calcium stearate, sodium stearyl fumarate and combinations can be used. Other suitable lubricants include one or more of polyethylene glycol (molecular weight above 3350), sodium lauryl sulfate, talc, mineral oil, leucine, and poloxamer.

In various aspects, the tablet can include a disintegrant. The disintegrant can be included in the formulation. The disintegrant can be the same as or different from the binder. By way of example and not limitation, microcrystalline cellulose has both binder and disintegrant properties and microcrystalline cellulose can be use as the sole binder/disintegrant in the formulation. Examples of other suitable disintegrants include croscarmellose sodium, crospovidone, sodium starch glycolate, and starch.

The binder can be present in the formulation in an amount ranging from approximately 4.5% by weight to approximately 30% by weight. The disintegrant can be present in the formulation in an amount ranging from approximately 1.5% by weight to approximately 15% by weight. In various embodiments, some non-starch disintegrants are often used at lower ranges, e.g., as low as 0.25% and thus the disintegrant present in the formulation can be as low as 0.25% in some conditions.

The lubricant can be present in the formulation in an amount ranging from approximately 0.5% by weight to approximately 3% by weight. It should be understood that some components, such as microcrystalline cellulose, can function with both disintegrant and binder properties.

The weight of individual tablets can depend upon the final dosage to be produced; e.g. 125 mg, 250 mg, 500 mg, 667 mg, 750 mg and 1,000 mg of ferric citrate.

In various embodiments, tablets are coated to a weight gain of approximately 2% to 5% using an Opadry® suspension or equivalent in a perforated pan coater. As noted above, calcium stearate and Opadry® purple can be replaced with or used with a different lubricant or coating system, respectively.

Tablets Having High Surface Area Per Unit Mass

In one variation, the disclosed tablets are made from granules having a significantly higher mean surface area per unit mass than previous ferric citrate formulations. It has been discovered that the increased surface area per unit volume results in immediate release dissolution times (greater than 80% at 60 minutes after administration as determined by United States Pharmacopeia (USP) test <711>, described in United States Pharmacopeia Compendium of Standards, USP 30 NF 25, Vol. 1 p. 276-284 (2007), which is incorporated herein by reference in its entirety). Without wishing to be limited to a specific theory or mode of action, the increased granular surface area of granules in the tablet results in an increased amount of ferric citrate exposed to the solvent. The immediate release dissolution times are significantly reduced in a reduced tablet size.

In additional variations, the tablets disclosed herein can be designed to have a mean granule particle surface area to mass ratio equal to or greater than 1 square meter per gram. In further variations, the tablet has a mean granule particle surface area to mass ratio equal to or greater than 2 square meters per gram. In further variations, the formulation has a mean granule particle surface area to mass ratio equal to or greater than 4 square meters per gram. In further variations, the formulation has a mean granule particle surface area to mass ratio equal to or greater than 6 square meters per gram. In further variations, the formulation has a mean granule particle surface area to mass ratio equal to or greater than 8 square meters per gram. In further variations, the formulation has a mean granule particle surface area to mass ratio equal to or greater than 10 square meters per gram. In further variations, the formulation has a mean granule particle surface area to mass ratio equal to or greater than 15 square meters per gram. In further variations, the formulation has a mean granule particle surface area to mass ratio equal to or greater than 20 square meters per gram. In further variations, the formulation has a mean granule particle surface area to mass ratio equal to or greater than 30 square meters per gram. In further variations, the formulation has a mean granule particle surface area to mass ratio equal to or greater than 40 square meters per gram. In further variations, the formulation has a mean granule particle surface area to mass ratio equal to or greater than 50 square meters per gram. The increased surface area per particle in a tablet resulted in a significantly increased dissolution rate.

In other variations, the tablets have reduced water content. In one embodiment, the granulation water content as measured by LOD % is less than 20%. In another embodiment, the granulation water content as measured by LOD % is less than 19%. In another embodiment, the granulation water content as measured by LOD % is less than 18%. In another embodiment, the granulation water content as measured by LOD % is less than 17%. In another embodiment, the granulation water content as measured by LOD % is less than 16%. In another embodiment, the granulation water content as measured by LOD % is less than 15%. In another embodiment, the granulation water content as measured by LOD % is less than 14%. In another embodiment, the granulation water content as measured by LOD % is less than 13%. In another embodiment, the granulation water content as measured by LOD % is less than 12%. In another embodiment, the granulation water content as measured by LOD % is less than 11%. In another embodiment, the granulation water content as measured by LOD % is less than 10%. In another embodiment, the granulation water content as measured by LOD % is less than 9%. In another embodiment, the granulation water content as measured by LOD % is less than 8%. In another embodiment, the granulation water content as measured by LOD % is less than 7%. In another embodiment, the granulation water content as measured by LOD % is less than 6%. In another embodiment, the granulation water content as measured by LOD % is less than 5%.

As will be understood to those of skill in the art, in various embodiments LOD is a method of thermogravimetric moisture determination: In thermogravimetric processes the moisture of a material includes substances that volatilize during warming, and therefore contribute to the material's loss of mass. Alongside water this may also include alcohol or decomposition products. When using thermogravimetric measurement methods (drying using infrared, halogen, microwaves or ovens) no distinction is made between water and other volatile components.

Friability

Friability generally measures the mechanical strength of tablets. During the process of coating, transportation, packing, and other processes, tablets can lose weight. To measure the weight loss the samples are counted and weighed.

In various embodiments, a friability test is performed as described in United States Pharmacopeia Compendium of Standards (2007), which is incorporated herein by reference in its entirety.

Chapter <1216> of the United States Pharmacopeia Compendium of Standards (2007) regarding tablet friability is recited below:

This general information chapter has been harmonized with the corresponding texts of the European Pharmacopoeia and the Japanese Pharmacopoeia. The harmonized texts of these three pharmacopeias are therefore interchangeable, and the methods of the European Pharmacopoeia and/or the Japanese Pharmacopoeia may be used for demonstration of compliance instead of the present United States Pharmacopeia general information chapter method. These pharmacopeias have undertaken not to make any unilateral change to this harmonized chapter.

This chapter provides guidelines for the friability determination of compressed, uncoated tablets. The test procedure presented in this chapter is generally applicable to most compressed tablets. Measurement of tablet friability supplements other physical strength measurements, such as tablet breaking force.

Use a drum (the apparatus meeting these specifications is available from laboratory supply houses such as VanKel Technology Group, 13000 Weston Parkway, Cary, N.C. 27513, or from Erweka Instruments, Inc., 56 Quirk Road, Milford, Conn. 06460), with an internal diameter between 283 and 291 mm and a depth between 36 and 40 mm, of transparent synthetic polymer with polished internal surfaces, and subject to minimum static build-up (see FIG. 1 for a typical apparatus). One side of the drum is removable. The tablets arc tumbled at each turn of the drum by a curved projection with an inside radius between 75.5 and 85.5 mm that extends from the middle of the drum to the outer wall. The outer diameter of the central ring is between 24.5 and 25.5 mm. The drum is attached to the horizontal axis of a device that rotates at 25±1 rpm. Thus, at each turn the tablets roll or slide and fall onto the drum wall or onto each other. For tablets with a unit weight equal to or less than 650 mg, take a sample of whole tablets corresponding as near as possible to 6.5 g. For tablets with a unit weight of more than 650 mg, take a sample of 10 whole tablets. The tablets should be carefully dedusted prior to testing. Accurately weigh the tablet sample, and place the tablets in the drum. Rotate the drum 100 times, and remove the tablets. Remove any loose dust from the tablets as before, and accurately weigh.

Generally, the test is run once. If obviously cracked, cleaved. or broken tablets are present in the tablet sample after tumbling, the sample fails the test. If the results are difficult to interpret or if the weight loss is greater than the targeted value, the test should be repeated twice and the mean of the three tests determined. A maximum mean weight loss from the three samples of not more than 1.0% is considered acceptable for most products.

If tablet size or shape causes irregular tumbling, adjust the drum base so that the base forms an angle of about 10° with the horizontal and the tablets no longer bind together when lying next to each other, which prevents them from falling freely.

Effervescent tablets and chewable tablets may have different specifications as tar as friability is concerned. In the case of hygroscopic tablets, an appropriate humidity-controlled environment is required for testing.

Drums with dual scooping projections, or an apparatus with more than one drum, for the running of multiple samples at one time, are also permitted.

Method of Making Tablets

In one tableting method, the tablets can be prepared in three steps. First, granules of ferric citrate and binder are formed. Second, a lubricant is added to the formulation before tableting. Third, the tablet is dried after an optional coating step.

Granulation

Ferric citrate, such as pharmaceutical grade ferric citrate described, for example, in U.S. Pat. No. 6,903,235 B2, can be granulated by any method known in the art. Exemplary methods of granulation include fluid bed granulation, high shear granulation and direct compression granulation.

In embodiments in which the moisture of the formulation was brought to the level above 25% LOD at any point resulted in a substantially lower surface area per gram of particle. This can be accomplished, for example, by limiting the quantity of water introduced, or by air blowing and monitoring the amount of water in a formulation.

To increase the surface area to mass ratio of ferric citrate particles to greater than 1 square meter per gram, or in other embodiments greater than 10 square meter per gram, the moisture content of the granules is maintained below 25% LOD throughout formation of granules. In certain variations, the moisture content of the granules is maintained at below 24% LOD, 23% LOD, 22% LOD, 21% LOD, or 20% LOD, throughout formation of granules.

Without wishing to be held to a particular mechanism or mode of action, it is hypothesized that keeping the amount of water below 25% LOD during granulation maintains granules with a high surface area per mass ratio. The addition of water in higher amounts at any time during the granulation process results in formation of larger granules with a lower mean surface area to mass ratio. The lower surface area to mass reduces the dissolution rate below the rate for an immediate release formulation. The measured lower mean surface area to mass ratio of granules results in slower dissolution and release characteristics.

In various embodiments, it has been observed that the reduced surface area to weight ratio of the ferric citrate formulation is irreversible after addition of moisture at above 25% LOD. Accordingly, the percent water is kept below 25% during granulation in various embodiments.

Blending

In various embodiments, one or more lubricants can be blended with the granules. In various embodiments, a non-limiting list of lubricants includes stearates such as calcium stearate and magnesium stearate, sodium stearyl fumarate, stearic acid, talc, polyethylene glycol, hydrogenated vegetable oils, aluminum stearate, sodium benzoate, sodium acetate, sodium chloride, leucine, Carbowax, and magnesium lauryl sulfate. Certain starches, such as Starch 1500, can also be considered lubricants, as they have some lubricant properties when used in direct compression application. Any lubricant known in the art can be used, including any of those disclosed in the Handbook of Pharmaceutical Excipients fifth edition, incorporated herein by reference in its entirety. Multiple lubricants can be combined.

In certain embodiments, a greater quantity of lubricant than is ordinarily used in the art can be used. It has been discovered that surprisingly, the quantity of lubricant must be higher than recommended or understood in the industry to reduce the quantity of sticking in the ferric citrate tablets.

In certain variations, a combination of magnesium or calcium stearate and sodium stearyl fumarate is used as a lubricant. In further embodiments, the lubricant is a combination of calcium stearate and sodium stearyl fumarate. In various embodiments, a greater quantity of calcium stearate than is recommended in the art can be used. As described in the Handbook of Pharmaceutical Excipients fifth edition, the recommended quantity of calcium stearate is a maximum of 1.0% w/w. In one embodiment, the quantity of calcium stearate is equal to or greater than 2.0% w/w. In another embodiment, the quantity of calcium stearate is equal to or greater than 2.2% w/w. In another embodiment, the quantity of calcium stearate is equal to or greater than 2.4% w/w.

Likewise, in various embodiments, a greater quantity of sodium stearyl fumarate than the recommended 0.5-2.0% w/w concentration can be used. In one embodiment, the quantity of sodium stearyl fumarate is greater than or equal to 2.1% w/w. In another embodiment, the quantity of sodium stearyl fumarate is greater than or equal to 2.2% w/w. In another embodiment, the quantity of sodium stearyl fumarate is greater than or equal to 2.3% w/w. In another embodiment, the quantity of sodium stearyl fumarate is greater than or equal to 2.4% w/w. In another embodiment, the quantity of sodium stearyl fumarate is greater than or equal to 2.5% w/w. In another embodiment, the quantity of sodium stearyl fumarate is greater than or equal to 2.6% w/w. In another embodiment, the quantity of sodium stearyl fumarate is greater than or equal to 2.7% w/w.

Post-Tableting Drying

A drying step can be performed after tableting. In the absence of drying the tablet after tableting, it was discovered that the dissolution rate of tablets increased over time. Drying maintained the immediate release characteristics of the ferric citrate tablets as disclosed herein. Without being limited to a specific mechanism or mode of action, it is believed that granule size increases due to the presence of residual water, and the drying step maintains the large surface area per unit weight of the original granules.

In one embodiment, the final granulation water content as measured by LOD % is less than 20%. In another embodiment, the final granulation water content as measured by LOD % is less than 19%. In another embodiment, the final granulation water content as measured by LOD % is less than 18%. In another embodiment, the final granulation water content as measured by LOD % is less than 17%. In another embodiment, the final granulation water content as measured by LOD % is less than 16%. In another embodiment, the final granulation water content as measured by LOD % is less than 15%. In another embodiment, the final granulation water content as measured by LOD % is less than 14%. In another embodiment, the final granulation water content as measured by LOD % is less than 13%. In another embodiment, the final granulation water content as measured by LOD % is less than 12%. In another embodiment, the final granulation water content as measured by LOD % is less than 11%. In another embodiment, the final granulation water content as measured by LOD % is less than 10%. In another embodiment, the final granulation water content as measured by LOD % is less than 9%. In another embodiment, the final granulation water content as measured by LOD % is less than 8%. In another embodiment, the final granulation water content as measured by LOD % is less than 7%. In another embodiment, the final granulation water content as measured by LOD % is less than 6%. In another embodiment, the final granulation water content as measured by LOD % is less than 5%.

EXAMPLES

The following examples describe the preparation and properties of various dosage forms and methods described herein. It will be apparent to those skilled in the art that many modifications, both to materials and methods, can be practiced without departing from the scope of the disclosure.

Example 1

The following exemplary formulations and formulation techniques for ferric citrate provide data showing characteristics for the formulations or tablets, including data such as dissolution, disintegration, and friability.

The sources for some of the materials included: ferric citrate from Biovectra; silicified microcrystalline cellulose (Prosolv SMCC 50 and Prosolv SMCC HD90 which is composed of microcrystalline cellulose, NF and colloidal silicon dioxide, NF) from JRS Pharma; pregelatinized starch, NF (Starch 1500) from Colorcon; Povidone, NF (Plasdone K-29/32) from ISP; hydroxypropyl cellulose, NF (Klucel EF) from Hercules; croscarmellose sodium, NF (Ac-Di-Sol SD-711) from FMC Biopolymer; and magnesium stearate, NF from Mallinckrodt.

The equipment used for the formulations included: FLM1 fluid bed from Vector Corporation of Marion, Iowa; Comil conical mill from Quadro Engineering of Millburn, N.J.; GMX high shear granulator 4 L bowl from Vector Corporation of Marion, Iowa; 2 qt V-blender from Patterson Kelley of East Stroudsburg, Pa.; XL100 Pro tablet press from Korsch of South Easton, Mass.; capsule-shaped tooling from Elizabeth Carbide of Lexington, N.C.; and Sonic sifter separator from Advantech Manufacturing of New Berlin, Wis.

The equipment used for the analytical testing of the formulations included: 8M Tablet Tester (hardness tester) from Dr. Schleuniger of Manchester, N.H.; Friabilator from VanKel of Palo Alto, Calif.; Flodex from Hanson Research of Chatsworth, Calif.; Bathless Disintegration System, Model 3106 and Bathless Dissolution System, Evolution 6100 from Distek of North Brunswick, N.J.; and Model 8453 UV-Vis from Agilent of Santa Clara, Calif.

High Shear Granulation

A series of experiments were conducted to determine the ability to use a high shear granulator to make a tablet blend having suitable characteristics. Formulations 1-3 are shown below in Tables 1-3.

TABLE 1

(Formulation 1)

| Component | mg/tablet | % w/w |
|---|---|---|
| Milled ferric citrate | 1190.3 | 75.0 |
| Silicified microcrystalline cellulose (Prosolv SMCC 50) | 238.1 | 15.0 |
| Croscarmellose sodium | 47.6 | 3.0 |
| Hydroxypropyl cellulose | 95.2 | 6.0 |
| Magnesium stearate | 15.9 | 1.0 |
| Total | 1587.0 | 100.0 |

TABLE 2

(Formulation 2)

| Component | mg/tablet | % w/w |
|---|---|---|
| Milled ferric citrate | 1190.4 | 60.0 |
| Silicified microcrystalline cellulose (Prosolv SMCC 50) | 595.2 | 30.0 |
| Croscarmellose sodium | 59.5 | 3.0 |
| Hydroxypropyl cellulose | 119.0 | 6.0 |
| Magnesium stearate | 19.8 | 1.0 |
| Total | 1984.0 | 100.0 |

TABLE 3

(Formulation 3)

| Component | mg/tablet | % w/w |
|---|---|---|
| Milled ferric citrate | 1190.3 | 69.0 |
| Silicified microcrystalline cellulose (Prosolv SMCC 50) | 258.8 | 15.0 |
| Croscarmellose sodium | 86.3 | 5.0 |
| Hydroxypropyl cellulose | 172.5 | 10.0 |
| Magnesium stearate | 17.3 | 1.0 |
| Total | 1725.0 | 100.0 |

The manufacturing procedure for the Formulations 1-3 was as follows.

Milled ferric citrate, hydroxypropyl cellulose, silicified microcrystalline cellulose, and croscarmellose sodium were mixed for 2 minutes at 500 rpm in a GMX high shear granulator 4 L bowl. Deionized water was added at an approximate rate of 18 g/min over 10 minutes, while mixing at a rate of 900 rpm with a chopper speed of 1500 rpm. The final (peak) moisture content was measured to be 24.3%, 23.8%, and 24.4%, respectively. The granules were dried in an FLM1 fluid bed for 5-8 minutes at an inlet temperature of 65° C. The moisture content after drying was measured to be 14.3%, 15.5%, and 15.9%, respectively. The granules were screened through a 16 mesh hand-screen, then through a 25 mesh hand screen to remove over-sized granules and clumps. The magnesium stearate was screened through a 25 mesh hand-screen. Granules and magnesium stearate were blended for 2 minutes in a 2 quart v-blender. Tableting was performed on a Korsch tablet press with capsule shaped tooling.

It was found that the resulting tablet blends demonstrated poor flow through the hopper due to the irregular particle shape of the granules. Nonetheless, excellent tablets were made using the tableting equipment.

Example 2

Another series of experiments were conducted to determine whether a tablet could be formulated using a fluid bed granulation process:

TABLE 4

(Formulations 4 and 5)

| Component | mg/tablet | % w/w |
|---|---|---|
| Milled ferric citrate | 1190.7 | 90.0 |
| Pregelatinized starch | 119.1 | 9.0 |
| Magnesium stearate | 13.2 | 1.0 |
| Total | 1323.0 | 100.0 |

The manufacturing procedure for Formulations 4 and 5 depicted in Table 4 are provided below as follows:

Milled ferric citrate was added to an FLM1 fluid bed granulator. For Formulation 4, pregelatinized starch was added as a 10% w/w solution at a spray rate that increased from 24 g/min to 52 g/min over the duration of the run. [Inlet Temp=64-77° C.; Product Temp=25-35° C.; Process Air=29-35 CFM]. The final (peak) moisture content was measured to be 32.5%.

For Formulation 5, pregelatinized starch was added as a 10% w/w solution at an average spray rate of 40.8 g/min. [Inlet Temp=69-75° C.; Product Temp=25-35° C.; Process Air=24-38 CFM]. The final (peak) moisture content was measured to be 30.0%.

The granules were dried for 7-10 minutes at an inlet temperature of 65° C. The moisture content after drying was measured to be 15.5% and 16.7%. Granules were milled through a Comil equipped with a 45R screen and square impeller at 1500 rpm. The magnesium stearate was screened through a 25 mesh hand-screen. Granules and magnesium stearate were blended for two minutes in a two quart V-blended. Tableting was performed on a Korsch tablet press with capsule shaped tooling.

The primary difference between the tablets of Formulations 4 and 5 was the disintegration time. The tablets of Formulation 5 had a slower disintegration time than the tablets of Formulation 4. These prototypes had no flow problems during tableting.

The powder properties of Formulations 1-5 were characterized as shown in Tables 5 and 6. All blends had excellent flow properties as measured by the Flodex.

TABLE 5

Powder Characterization of High Shear Blends

| Measurement | Formulation 1 | Formulation 2 | Formulation 3 |
|---|---|---|---|
| Bulk density | 0.772 g/mL | 0.618 g/mL | 0.679 g/mL |
| Flodex | 4 | 5 | 10 |

TABLE 6

Powder Characterization of Fluid Bed Blends

| Measurement | Formulation 4 | Formulation 5 |
|---|---|---|
| Bulk density | 0.647 g/mL | 0.578 g/mL |
| Flodex | 4 | 4 |

Experimental formulations of Formulations 1 and 5 were examined by Scanning Electron Microscopy (SEM) and both samples had a similar particle size range. While the particles of Formulation 1 appeared to have a bimodal distribution, both samples had distinct particle morphologies. Formulation 1, which was prepared by high shear granulation, had more sharp, oblong particles. Formulation 5, prepared by fluid bed granulation, had more soft, round particles. This difference is believed to have an impact on the flow properties observed during tableting.

Figure 2:
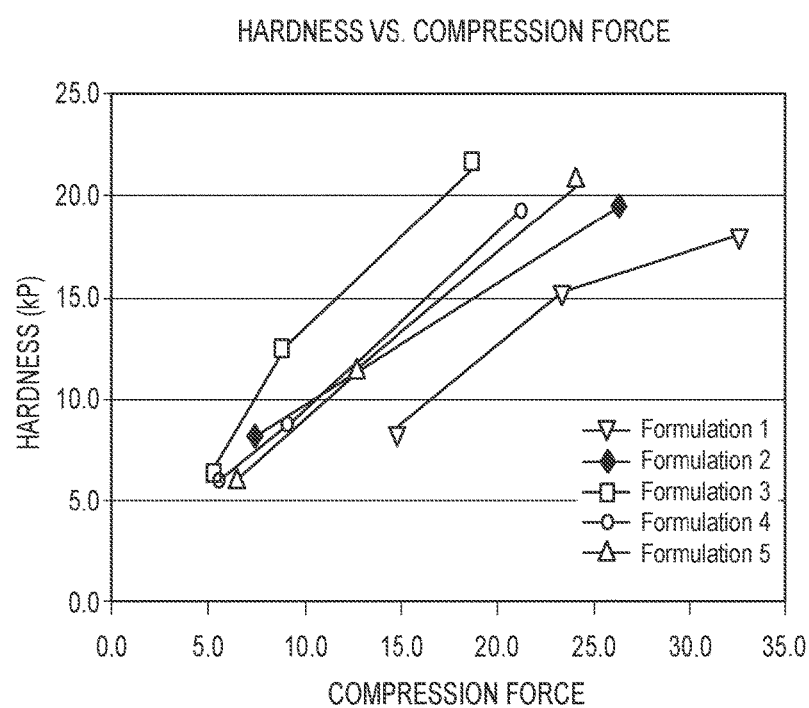
FIG. 2 is a chart showing hardness as a function of compression force for Formulations 1-5.
Figure 3:
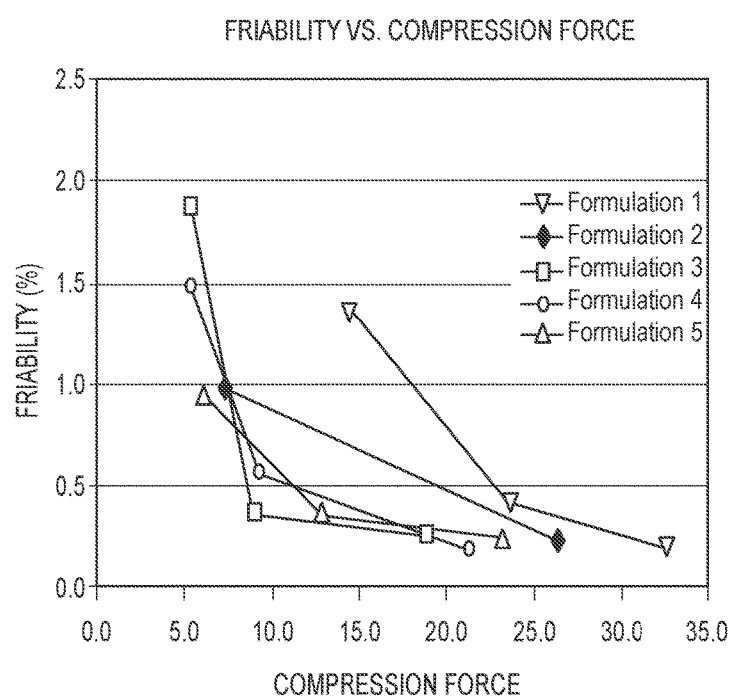
FIG. 3 is a chart showing friability as a function of compression force for Formulations 1-5.
Figure 4:
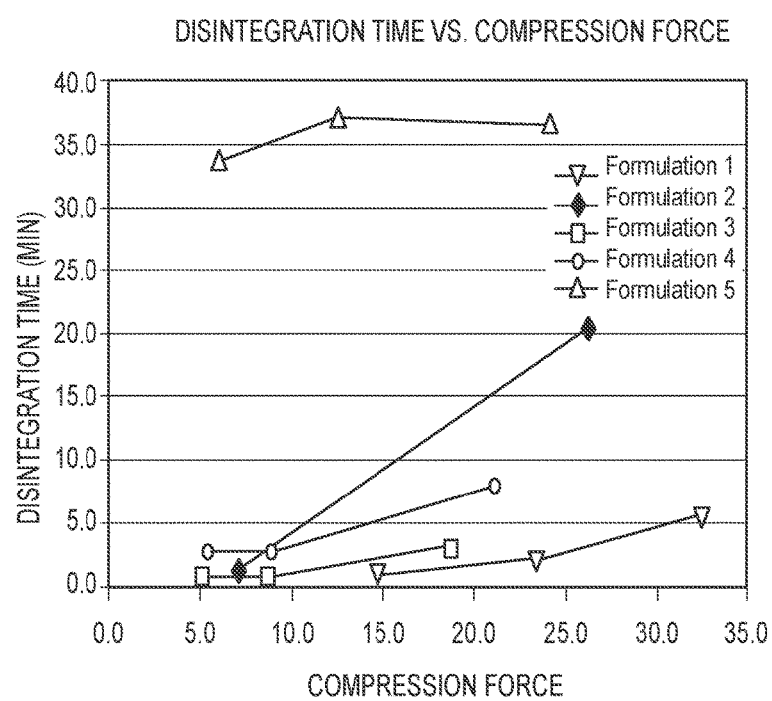
FIG. 4 is a chart showing disintegration time as a function of compression force for Formulations 1-5.
Figure 5:
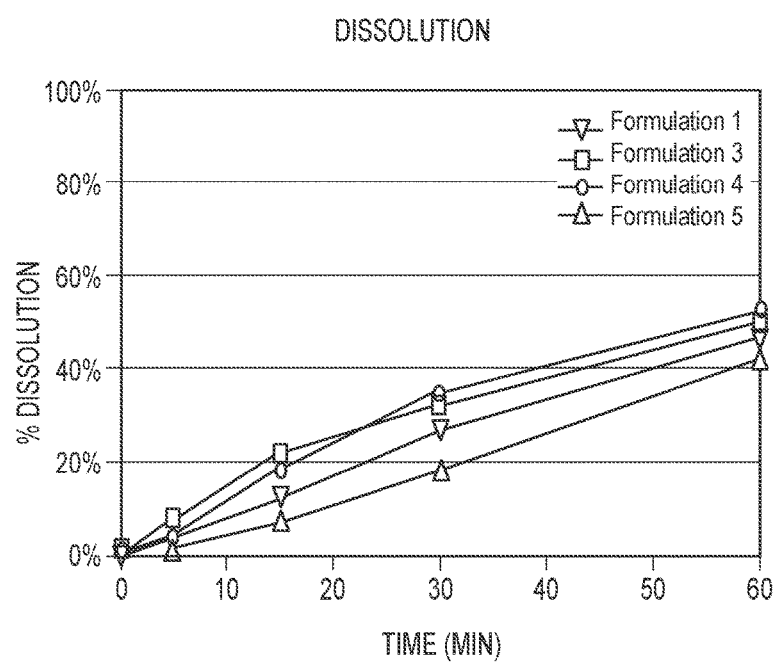
FIG. 5 is a chart showing dissolution time for Formulations 1 and 3-5.

The tablet properties of Formulations 1-5 were characterized as shown in Table 7 and Table 8. Compaction profiles were made of each formulation, graphically presented in FIG. 2 (hardness), FIG. 3 (friability), and FIG. 4 (disintegration). Characterization data is presented only of the tablets prepared at the highest compaction force. Compression force is measured in kilo Newtons. Dissolution results are graphically presented in FIG. 5 for Formulations 1 and 3-5.

For the hardness testing, the tablets were tested according to USP <1217> for hardness/breaking strength. For the friability testing, the tablets were tested following USP <1216> for friability. For the disintegration testing, six tablets were tested using a disintegration apparatus in deionized water at 37° C. For the dissolution testing, six tablets were tested for dissolution properties according to the conditions listed below. Tablet dissolution results were scaled to report 100% dissolution as a 1000 mg dose, correcting for actual average tablet weight, as needed.

Dissolution Conditions:
Dissolution Instrument: Distek Evolution 6100
Medium: pH 4.0 McIlvaine buffer
Apparatus USP: Apparatus II (paddle method); 100 rpm
Temperature: 37° C.±0.5° C.
Time: Samples taken at 5, 15, 30, and 60 minutes
UV-Vis Instrument: Agilent 8453 UV-Vis; 360 nm with 600 nm background correction.

TABLE 7

Characterization of High Shear Experiments (Formulations 1-3)

| Measurement | Formulation 1 | Formulation 2 | Formulation 3 |
|---|---|---|---|
| Weight variation | Average 1580.8 mg (0.5% RSD) | Average 1485.6 mg (0.4% RSD) | Average 1518.4 mg (0.7% RSD) |
| Thickness | Average 8.59 mm (0.2% RSD) | Average 8.37 mm (0.2% RSD) | Average 8.69 mm (0.4% RSD) |

TABLE 7-continued

Characterization of High Shear Experiments (Formulations 1-3)

| Measurement | Formulation 1 | Formulation 2 | Formulation 3 |
|---|---|---|---|
| Hardness | 18.1 kp (2.6% RSD) | 19.5 kp (2.3% RSD) | 21.5 kp (3.8% RSD) |
| Friability | 0.19% | 0.22% | 0.26% |
| Disintegration | Average 5.8 minutes | Average 19.8 minutes | Average 3.0 minutes |
| Dissolution | 48.2% in 60 minutes | — | 49.7% in 60 minutes |

TABLE 8

Tablet Characterization of Fluid Bed Experiments (Examples 4 and 5)

| Measurement | Formulation 4 | Formulation 5 |
|---|---|---|
| Weight variation | Average 1286.5 mg (0.3% RSD) | Average 1313.2 mg (0.4% RSD) |
| Thickness | Average 7.18 mm (0.2% RSD) | Average 7.24 mm (0.2% RSD) |
| Hardness | Average 19.3 kp (3.2% RSD) | 20.5 kp (7.4% RSD) |
| Friability | 0.20% | 0.23% |
| Disintegration | Average 7.7 minutes | Average 36.3 minutes |
| Dissolution | 50.4% in 60 minutes | 42.5% in 60 minutes |

For the high shear prototypes (Formulations 1-3) incorporation of increased silicified microcrystalline cellulose (Formulation 1 and Formulation 2) improved compactibility, as shown by reduced compression forces required to achieve equivalent hardness. Also, incorporation of increased hydroxypropyl cellulose (Formulations 1, 2, and 3) improved compactibility, as shown by reduced compression forces required to achieve equivalent hardness.

Example 3

Additional development was conducted to achieve a balance between dissolution profile and acceptable tablet properties. The fluid bed granulation spray rate was varied step-wise using pregelatinized starch, which showed that in-process moisture content plays a role in dissolution profile and tablet properties.

Fluid Bed Granulation with Starch

Batches of Formulations 6-11 shown in Tables 9 and 10 were prepared using pregelatinized starch with target batch sizes of 1.0 kg.

TABLE 9

Formulation Formulations 6-8

| Component | mg/tablet | % w/w |
|---|---|---|
| Milled ferric citrate | 1190.7 | 90.0 |
| Pregelatinized starch | 119.1 | 9.0 |
| Magnesium stearate | 13.2 | 1.0 |
| Total | 1323.0 | 100.0 |

TABLE 10

Formulation Formulations 9-11

| Component | mg/tablet | % w/w |
|---|---|---|
| Milled ferric citrate | 1190.7 | 80.9 |
| Pregelatinized starch | 119.1 | 8.1 |
| Silicified microcrystalline cellulose | 147.2 | 10.0 |
| Magnesium stearate | 13.2 | 1.0 |
| Total | 1470.2 | 100.0 |

Formulations 6-11 were manufactured as follows:

Milled ferric citrate was added to an FLM1 fluid bed granulator. Pregelatinized starch was added as a 10% w/w solution using the granulation and drying parameters in Table 11. All batches were dried at an inlet temperature of 65° C.

TABLE 11

Granulation Parameters

| Parameter | Formulation 6 and 9 | Formulations 7 and 10 | Formulations 8 and 11 |
|---|---|---|---|
| Spray rate | 24.0 g/min | 32.5 g/min | 37.5 g/min |
| Inlet temp | 69-79° C. | 72-75° C. | 69-76° C. |
| Product temp | 26-35° C. | 26-36° C. | 26-35° C. |
| Process air | 31-36 CFM | 32-38 CFM | 36-39 CFM |
| Final (peak) moisture | 17.3% | 23.4% | 25.7% |
| Moisture after drying | 14.8% | 16.1% | 17.5% |
| Drying time | 2 minutes | 5 minutes | 7 minutes |

Granules from Formulations 6, 7, 9 and 10 were screened through a 20 mesh hand-screen. Granules from Formulations 8 and 11 were milled through a Comil equipped with a 45R screen and square impeller at 1500 rpm, then screened through a 20 mesh hand-screen.

Two blends were prepared from each granulation. In the first blend, the magnesium stearate was screened through a 25 mesh hand-screen. Granules and magnesium stearate were blended for two minutes in a two quart V-blender. In the second blend, the magnesium stearate was screened through a 25 mesh hand-screen. Granules, silicified microcrystalline cellulose, and magnesium stearate were blended for two minutes in a two quart V-blender.

Tableting was performed on a Korsch tablet press with capsule shaped tooling on several of the prepared blends.

The resulting tablets of Formulations 6 and 9 had flow properties with Hausner ratio values equal to or less than 1.25 and/or Carr index values equal to or less than 25. In various embodiments, the Hauser ratio is equal to or less than 1.20. In further embodiments, the Hauser ratio is equal to or less than 1.20. In various embodiments, the Carr index is less than 25. In further embodiments, the Carr index is equal to or less than 20.

Excellent flow: Hausner ratio values about or less than 1.20 and Carr index values less than 20 showed evidence that additional lubrication was needed to achieve better tableting results. The resulting tablets of Formulations 7, 8, 10 and 11 had excellent flow properties and made successful tablets.

The powder properties of Formulations 6-11 were characterized as shown in Table 12. Formulations 7, 8, 10 and 11 have flow properties with Hauser ratios equal to or less than 1.20 and Carr index values less than 20 as measured by the Flodex, presumably due to the higher spray rates of those experiments. The bulk density of the starch granulation experiments increased as the spray rate increased.

TABLE 12

Powder Characterization of Fluid Bed Experiments

| Measurement | Formulations 6 and 9 | Formulations 7 and 10 | Formulations 8 and 11 |
|---|---|---|---|
| Bulk density | 0.475 g/mL | 0.531 g/mL | 0.698 g/mL |
| Flodex | 7 | 4 | 4 |

Figure 6:
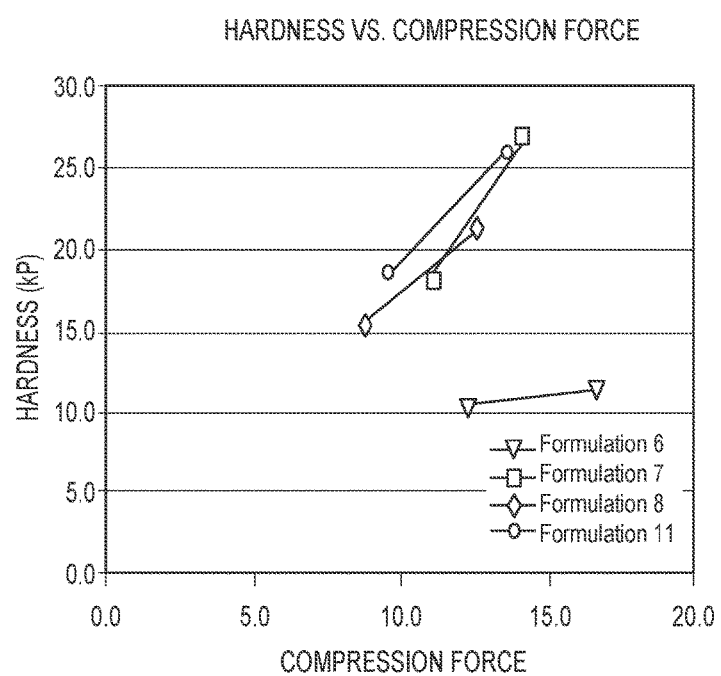
FIG. 6 is a chart showing hardness as a function of compression force for Formulations 6-8 and 11.
Figure 7:
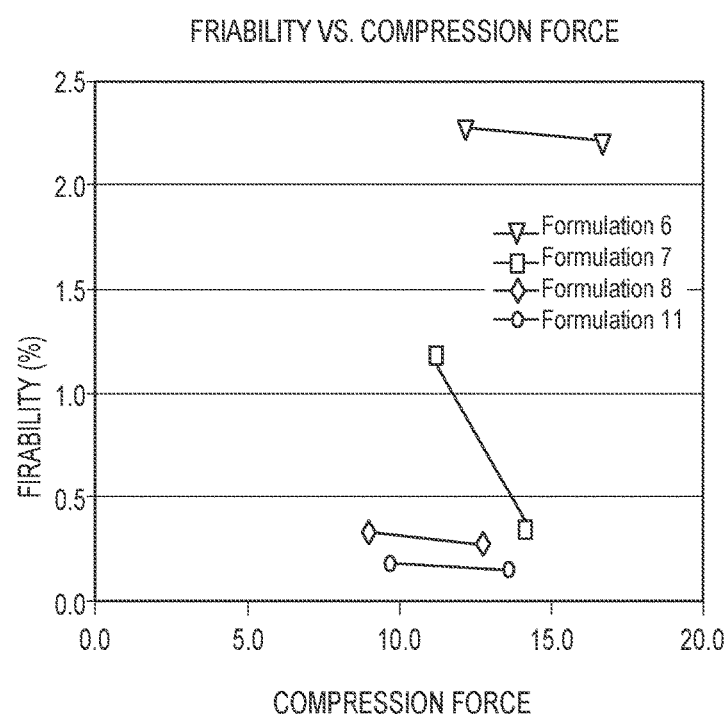
FIG. 7 is a chart showing friability as a function of compression force for Formulations 6-8 and 11.
Figure 8:
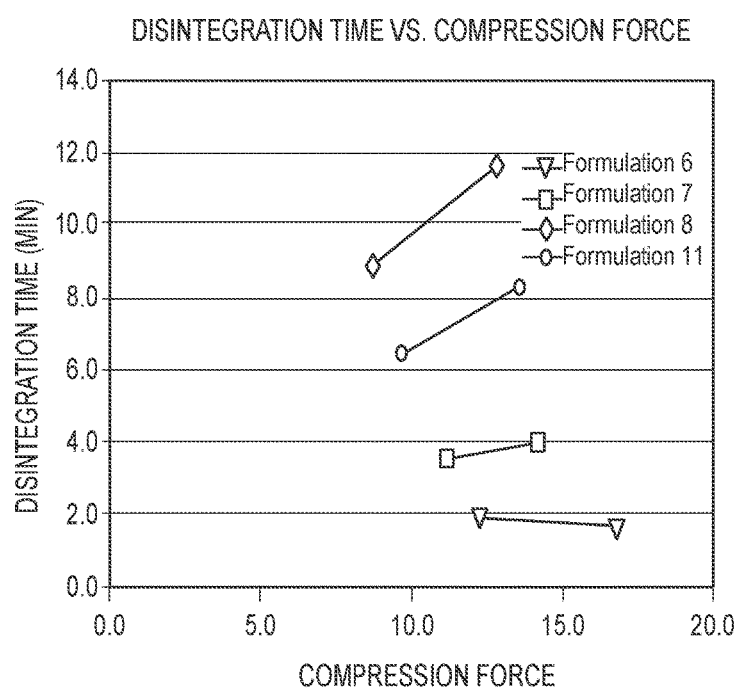
FIG. 8 is a chart showing disintegration time as a function of compression force for Formulations 6-8 and 11.
Figure 9:
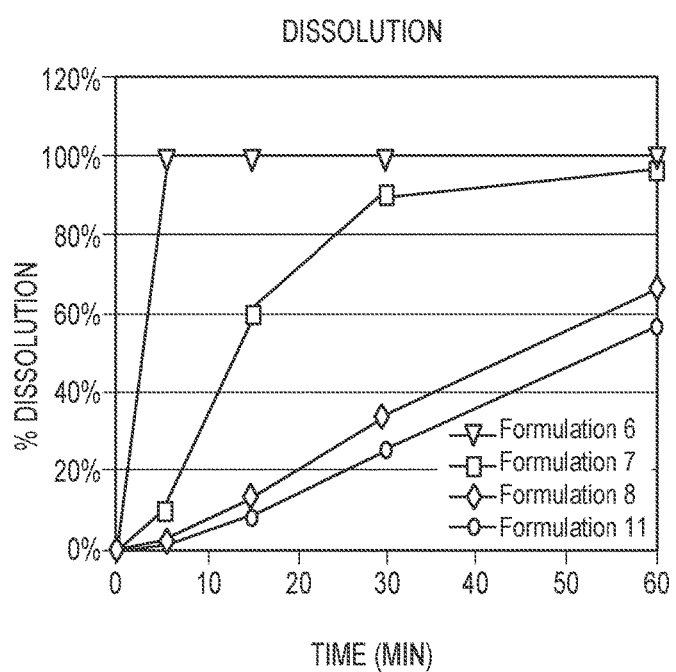
FIG. 9 is a chart showing dissolution time for Formulations 6-8 and 11.

The tablet properties of Formulations 6-8 and 11 were characterized as shown in Table 13 and 14. Compaction profiles were made for each formulation and are graphically presented in FIG. 6 (hardness), FIG. 7 (friability) and FIG. 8 (disintegration). Characterization data is presented only of the tablets prepared at the highest compaction force. Dissolution results are graphically presented in FIG. 9 for Formulations 6-8 and 11.

TABLE 13

Tablet Characterization of Fluid Bed Formulations 6 and 7

| Measurement | Formulation 6 | Formulation 7 |
|---|---|---|
| Weight variation | Average 1126.9 mg (0.4% RSD) | Average 1272.8 mg (0.4% RSD) |
| Thickness | Average 7.74 mm (0.2% RSD) | Average 8.00 mm (0.5% RSD) |
| Hardness | Average 11.2 kp (28.7% RSD) | 27.2 kp (8.9% RSD) |
| Friability | 2.23% | 0.36% |
| Disintegration | Average 1.8 minutes | Average 3.9 minutes |
| Dissolution | 99.9% in 60 minutes | 95.7% in 60 minutes |

TABLE 14

Tablet Characterization of Fluid Bed Formulations 8 and 11

| Measurement | Formulation 8 | Formulation 11 |
|---|---|---|
| Weight variation | Average 1332.0 mg (0.3% RSD) | Average 1497.7 mg (0.3% RSD) |
| Thickness | Average 7.94 mm (0.1% RSD) | Average 8.72 mm (0.1% RSD) |
| Hardness | Average 21.1 kp (2.8% RSD) | 26.1 kp (2.9% RSD) |
| Friability | 0.28% | 0.15% |
| Disintegration | Average 11.7 minutes | Average 8.3 minutes |
| Dissolution | 55.8% in 60 minutes | 65.6% in 60 minutes |

Milled ferric citrate and croscarmellose sodium were added to an FLM1 fluid bed. Povidone was added as a 30% w/w solution (Formulation 12) and 20% w/w solution (Formulation 13) using the granulation and drying parameters in Table 15 to make granules. No drying was required.

TABLE 15

Granulation Parameters

| Parameter | Formulation 12 | Formulation 13 |
|---|---|---|
| Spray rate | 22.9 g/min | 30.0 g/min |
| Inlet temp | 55-60° C. | 52-58° C. |
| Product temp | 31-37° C. | 22-30° C. |
| Process air | 31-36 CFM | 35-38 CFM |
| Final (peak) moisture | 13.0% | 17.3% |

Granules were screened through a 20 mesh hand-screen. The magnesium stearate was screened through a 25 mesh hand-screen. Granules and magnesium stearate were blended for two minutes in a two quart V-blender.

Tableting was performed on a Korsch tablet press. During the tableting process, there was excessive sticking to the tooling. This sticking was believed to be addressable by use of different tooling or by varying the tableting parameters.

Example 4

Additional examples were formulated and analyzed. A summary of the results are provided below in Tables 16 and 17. Table 16 provides a summary of results for Formulations 14-20 using direct compression of the formulations. Table 17 provides a summary of results for Formulations 21-29 using fluid bed granulation. These various formulations showed a variety of ranges of properties that could be useful depending upon the application, e.g., immediate release, extended release, and delayed release, with a minor amount of additional experimentation required for some of the formulations to ensure that suitable tablets are formed.

TABLE 16

Qualitative Results for Direct Compression Formulations

| Experiment Reference | Dose Target | Formulation Summary | Results and Observations |
|---|---|---|---|
| Formulation 14 | 667 mg | 91.9% Ferric Citrate, 7.3% Prosolv SMCC 50, 0.8% Magnesium Stearate | Tablets had some lamination, achieved 12.5 kp average hardness |
| Formulation 15 | 667 mg | 91.9% Ferric Citrate, 7.3% Prosolv HD 90, 0.8% Magnesium Stearate | Friability equal to or less than 1.0% w/w. |
| Formulation 16 | 667 mg | 87.0% Ferric Citrate, 7.3% Prosolv SMCC 50, 4.9% Povidone K-29/32, 0.8% Magnesium Stearate | Friability equal to or less than 1.0% w/w. |
| Formulation 17 | 500 mg | 90.7% Ferric Citrate, 8.5% Prosolv HD 90, 0.8% Magnesium Stearate | Tablets showed capping and lamination addressable with additional binder or varying the tableting parameters |

TABLE 16-continued

Qualitative Results for Direct Compression Formulations

| Experiment Reference | Dose Target | Formulation Summary | Results and Observations |
|---|---|---|---|
| Formulation 18 | 500 mg | 90.7% Ferric Citrate, 8.0% Prosolv HD 90, 0.5% Povidone K-29/32, 0.8% Magnesium Stearate | Tablets showed capping and lamination addressable with additional binder or varying the tableting parameters; long disintegration times |
| Formulation 19 | 500 mg | 88.0% Ferric Citrate, 7.0% Avicel PH 200, 2.7% Povidone K-29/32, 1.5% Crospovidone XL, 0.8% Magnesium Stearate | Tablets showed capping and lamination addressable with additional binder or varying the tableting parameters; disintegration time reduced to 1-3 minutes suitable for immediate release applications |
| Formulation 20 | 500 mg | 87.0% Ferric Citrate, 7.0% Avicel PH 200, 3.7% Povidone K-29/32, 1.5% Crospovidone XL, 0.8% Magnesium Stearate | Tablets showed reduced lamination that was addressable with additional binder or varying the tableting parameters, disintegration time 3-5 minutes suitable for immediate release applications |

TABLE 17

Qualitative Results for Fluid Bed Granulation Formulations

| Experiment Reference | Dose Target | Formulation Summary | Results and Observations |
|---|---|---|---|
| Formulation 21 | 500 mg | 90.0% Ferric Citrate, 2.0% Povidone K-29/32, 2.0% Starch 1500, 5.2% Avicel PH 102, 0.8% Magnesium Stearate | Friability equal to or less than 1.0% w/w. |
| Formulation 22 | 500 mg | 90.0% Ferric Citrate, 4.0% Starch 1500, 5.2% Avicel PH 102, 0.8% Magnesium Stearate | Acceptable tablet properties with additional development work needed for tablet integrity |
| Formulation 23 | 500 mg | 90.0% Ferric Citrate, 9.0% Starch 1500, 1.0% Magnesium Stearate | Tablets had disintegration more than 15 minutes. |
| Formulation 24 | 500 mg | 90.0% Ferric Citrate, 4.0% Starch 1500, 5.2% Avicel PH 102, 0.8% Magnesium Stearate | Tablets had disintegration more than 15 minutes. |
| Formulation 25 | 500 mg | 80.0% Ferric Citrate, 8.0% Starch 1500, 11.0% Avicel PH 200, 1.0% Magnesium Stearate | Tablets had disintegration more than 15 minutes. |
| Formulation 26 | 500 mg | 90.0% Ferric Citrate, 9.0% Starch 1500, 1.0% Magnesium Stearate | Tablets had disintegration more than 15 minutes. |
| Formulation 27 | 500 mg | 85.0% Ferric Citrate, 8.5% Starch 1500, 5.5% Avicel PH 200, 1.0% Magnesium Stearate | Tablets had disintegration more than 15 minutes. |
| Formulation 28 | 1000 mg | 84.9% Ferric Citrate, 5.6% Starch 1500, 8.6% Avicel PH 200, 1.0% Magnesium Stearate | Granulation very dense |
| Formulation 29 | 1000 mg | 89.5% Ferric Citrate, 5.9% Starch 1500, 3.6% Avicel PH 200, 1.0% Magnesium Stearate | Acceptable tablet properties with tableting and coating successful |

Example 5

Tables 18a and 18b provide Formulations 30 and 31 for an exemplary ferric citrate drug product.

TABLE 18a

Formulation 30 for a Ferric Citrate Drug Product

| Material Description | Theoretical kg/Batch | % w/w |
|---|---|---|
| Ferric Citrate | 14.89 | 87.6 |
| Pregelatinized Starch | 1.70 | 10.0 |
| Calcium Stearate | 0.406 | 2.4 |
| Purified Water | 15.30* | N/A** |
| Core Tablet Total | 17.00 | 100.0 |
| Opadry Purple 03K100000 | 0.51 | 15.0 |
| Purified Water | 2.89* | 85.0** |
| Coated Tablet Total | 17.5 | 100.0 |

*Purified water is removed during the drying phase.

TABLE 18b

Formulation 31 for a Ferric Citrate Drug Product

| Material Description | Theoretical Kg/Batch | % w/w |
|---|---|---|
| Ferric Citrate | 14.87 | 85.0 |
| Silicified Microcrystalline Cellulose | 0.70 | 4.0 |
| Pregelatinized Starch | 1.58 | 9.0 |
| Calcium Stearate | 0.35 | 2.0 |
| Purified Water | 14.18 | N/A* |
| Core Tablet Total | 17.5 | 100.0 |
| Opadry Purple 03K100000 | 0.51* | 15.0 |
| Purified Water | 2.89* | 85.0** |
| Coated Tablet Total | 18.0 | 100.0 |

Table 19 provides a proposed ferric citrate drug product formulation that can be used in the manufacturing process described below.

TABLE 19

Formulation 32

| Material Description | Theoretical 100 kg/Lot | % w/w to Core Tablet | % w/w Coated Tablet |
|---|---|---|---|
| Ferric Citrate | 80.0-90.0 | 80.0-90.0 | 76.2-88.2 |
| Pregelatinized Starch | 8.0-15.0 | 8.0-15.0 | 7.6-14.7 |
| Calcium Stearate | 2.0-3.0 | 2.0-3.0 | 1.9-2.9 |
| Purified Water | N/A* | N/A* | N/A* |
| Core Tablet Total | 100.0 | 100.0 | N/A* |
| Opadry Purple 03K100000 | 5.3 | 15.0 | 2.0-5.0 |
| Purified Water | 30.0* | 85.0* | N/A* |
| Coated Tablet Total | 35.3 | 100.0 | 100.0 |

*Purified water is removed
(1) or other binders as listed in the patent
(2) or other lubricants as listed in the patent
(3) or other coating system as listed in the patent

Example 6

The drug product tablet was produced using fluid bed granulation of the screened API with a binder suspension of pregelatinized starch, targeting a moisture content after granulation of approximately 13-20%. The granulated active was subsequently blended with screened calcium stearate and the mix compressed to form a tablet core. The tablet was robust with friability equal to or less than 1.0% w/w, hardness from 8-20 kp, disintegration equal to or less than 15 min, and compression force about 3.5-5.0 kN, with a main force 5-20 kN. It will be recognized that various embodiments are within the ranges of one or more of each of these parameters.

The weight of individual tablets can depend upon the final dosage to be produced; e.g., 125 mg, 250 mg, 500 mg, 667 mg, 750 mg and 1,000 mg of ferric citrate. The process is capable of consistently producing tablets within a specification of ±5% of target. The tablet thickness and hardness meet the specified acceptance criteria. The tablets are coated to a target weight gain of approximately 2% to 5% using an Opadry® suspension or equivalent in a perforated pan coater.

The production results demonstrate the selected formulation and process are capable of producing robust tablets meeting the specified criteria. First, ferric citrate was passed through a screening mill. A granulation drug binder suspension was then prepared by adding purified water to a stainless steel mixing kettle, then adding pregelatinized starch to the purified water and mixing. Granulated particles were formed by screening ferric citrate through a fluid bed granulator. The pregelatinized starch binder suspension was sprayed into the fluidized product bed. At the completion of binder addition the granulation was dried.

The dried granules were charged into a diffusion mixer. Calcium stearate was screened and added to the granulation in the diffusion mixer. The granules and lubricant were mixed.

The lubricated granules were compressed into tablets. Tablets were collected in intermediate bulk containers. An aqueous film coating suspension was prepared in a stainless steel kettle and mixer. The tablets were charged into a fully perforated pan coater, and the coating suspension was sprayed onto the cascading product bed. Upon completion of the spraying step the tablets were dried. Film coated tablets were discharged into intermediate bulk containers. The film coated tablets were packaged in HPDE bottles with desiccant and child resistant foil induction seal cap.

Example 7

Ferric citrate tablets were formulated as described above. Tablet Formulations 33 and 34 are depicted in Tables 20 and 21.

TABLE 20

Formulation 33

| Material Description | Target kg/Batch | Theoretical 100 kg/Lot | % w/w Core Tablet | % w/w Coated Tablet |
|---|---|---|---|---|
| Ferric Citrate | 14.9 | 80.0-90.0 | 80.0-90.0 | 76.2-88.2 |
| Pregelatinized Starch | 1.7 | 8.0-15.0 | 8.0-15.0 | 7.6-14.7 |
| Calcium Stearate (1) | 0.4 | 1.0-3.0 | 1.0-3.0 | 0.9-2.9 |

TABLE 20-continued

Formulation 33

| Material Description | Target kg/Batch | Theoretical 100 kg/Lot | % w/w Core Tablet | % w/w Coated Tablet |
|---|---|---|---|---|
| OR - Sodium Stearyl Fumarate (1) | 0.4 | 2.0-3.0 | 2.0-3.0 | 1.9-2.9 |
| Purified Water | 15.3* | 72.0-135.0* | * | * |
| Core Tablet Total | 17.0 | 100.0 | 100.0 | N/A* |
| Opadry Purple | 0.9 | 5.3 | 15.0 | 2.0-5.0 |
| Purified Water | 5.1* | 30.0* | 85.0* | N/A* |
| Coated Tablet Total | 17.5 to 17.9 | 35.3 | 100.0 | 100.0 |

(1) - Either calcium stearate or sodium stearyl fumarate may be used as lubricant
*Purified water is removed

TABLE 21

Formulation 34

| Material Description | Target kg/Batch | Theoretical 100 kg/Lot | % w/w Core Tablet | % w/w Coated Tablet |
|---|---|---|---|---|
| Ferric Citrate | 14.9 | 80.0-90.0 | 80.0-90.0 | 76.2-88.2 |
| Pregelatinized Starch | 1.6 | 8.0-12.0 | 8.0-12.0 | 7.6-11.5 |
| Silicified Macrocrystalline Cellulose | 0.7 | 3.0-5.0 | 3.0-5.0 | 2.5-4.5 |
| Calcium Stearate (1) | 0.4 | 1.0-3.0 | 1.0-3.0 | 0.9-2.9 |
| OR - Sodium Stearyl Fumarate (1) | 0.4 | 2.0-3.0 | 2.0-3.0 | 1.9-2.9 |
| Purified Water | 15.3* | 72.0-135.0* | * | * |
| Core Tablet Total | 17.6 to 18.0 | 100.0 | 100.0 | N/A* |
| Opadry Purple 03K100000 | 0.9 | 5.3 | 15.0 | 2.0-5.0 |
| Purified Water | 5.1* | 30.0* | 85.0* | N/A* |
| Coated Tablet Total | 17.8 to 18.9 | 35.3 | 100.0 | 100.0 |

(1) - Either calcium stearate or sodium stearyl fumarate used as lubricant
*Purified water is removed

Example 8

A ferric citrate tablet was made under conditions in which granulation was conducted by allowing the LOD water % to increase above 25%.

Pharmaceutical grade ferric citrate was added into a fluid bed granulator. Pregelatinized starch binder suspension (Pregelatinized starch+water) was sprayed into the fluidized product bed. The water moisture level of the formulation was allowed to exceed 25% by LOD (loss on drying method).

In embodiments in which the moisture of the formulation was brought to the level above 25% LOD at any point resulted in a substantially lower surface area per gram of particle.

Referring to Table 22, the moisture provided during manufacturing increased above 20% at 120 minutes and increased to 27.89% at 170 minutes.

TABLE 22

Granulation Operating Parameters

| Time | Rate (g/min) | Pump Speed (rpm) | Inlet Air (scfm) | Inlet Temp (° C.) | Product Temp (° C.) | Atom Air (psi) | LOD (%) | Exhaust Temp (° C.) |
|---|---|---|---|---|---|---|---|---|
| 0 | — | — | 145 | 42 | 35.8 | 65.0 | 11.85 | 30.6 |
| 10 | 87.7 | 30 | 150 | 61.6 | 30.0 | 65.0 | 12.82 | 28.4 |
| 20 | 71.2 | 30 | 153 | 63.5 | 28.2 | 65.0 | 13.02 | 26.6 |
| 30 | 76.2 | 30 | 153 | 63.1 | 27.5 | 64.7 | 13.18 | 25.8 |
| 40 | 77.7 | 30 | 144 | 63 | 27.1 | 65.1 | 15.19 | 25.4 |
| 50 | 75.9 | 30 | 146 | 63.1 | 27.0 | 65.1 | 15.7.0 | 25.3 |
| 60 | 79.6 | 30 | 147 | 63.0 | 26.8 | 65.1 | 15.74 | 25.2 |
| 71 | 80.0 | 30 | 144 | 62.9 | 26.7 | 65.1 | — | 25.1 |
| 80 | 83.4 | 33 | 149 | 63.0 | 26.7 | 65.1 | 17.31 | 25.1 |
| 90 | 90.5 | 33 | 151 | 63.0 | 26.5 | 65.1 | 18.49 | 25.0 |
| 100 | 90.4 | 33 | 152 | 63.0 | 26.5 | 65.1 | 18.64 | 24.9 |
| 110 | 90.5 | 33 | 153 | 63.0 | 26.4 | 65.1 | 18.99 | 24.8 |
| 120 | 90.5 | 33 | 150 | 63.0 | 26.4 | 65.1 | 22.89 | 24.8 |
| 130 | 90.4 | 33 | 144 | 63.0 | 26.3 | 65.1 | 22.47 | 24.8 |
| 141 | 91.1 | 33 | 153 | 63.0 | 26.3 | 65.1 | 24.25 | 24.7 |
| 150 | 90.2 | 33 | 152 | 63.0 | 26.2 | 65.1 | 25.41 | 24.7 |
| 160 | 91.8 | 33 | 153 | 62.9 | 26.2 | 65.0 | 26.03 | 24.7 |
| 170 | 89.6 | 33 | 154 | 63.0 | 26.2 | 65.1 | 27.89 | 24.7 |
| 180 | 90.7 | 33 | 149 | 63.0 | 26.2 | 65.1 | 27.47 | 24.7 |
| 190 | — | — | 147 | 63.0 | 26.4 | — | 26.76 | 24.7 |
| 200 | — | — | 150 | 63.0 | 26.8 | — | 25.00 | 25.0 |
| 210 | — | — | 154 | 63.1 | 27.2 | — | 22.37 | 25.1 |
| 220 | — | — | 153 | 63.1 | 27.8 | — | 21.32 | 25.2 |
| 230 | — | — | 149 | 63.1 | 29.0 | — | 18.68 | 25.7 |
| 240 | — | — | 153 | 63.1 | 30.7 | — | 17.55 | 26.5 |
| | | | | | | Final LOD | 16.69 | |

The measured surface area of two samples prepared using the above formulation is depicted in Table 23. The surface areas of the formulations were 0.12 m$^2$/g and 0.20 m$^2$/g.

TABLE 23

| Sample | Sample 1 BET Surface Area (m$^2$/g) | Sample 2 BET Surface Area (m$^2$/g) |
|---|---|---|
| Pre-granulation(API + ProSolv) | 27.99 | 32.34 |
| PostGranulation | 0.12 | 0.20 |

The mean surface area per unit mass ratios of the two samples was 0.12 and 0.20 m$^2$/g, respectively.

Example 9

A ferric citrate tablet was prepared by keeping granules at an LOD % water concentration less than 25% during granulation.

Pharmaceutical grade ferric citrate was added into a fluid bed granulator. Pregelatinized starch binder suspension (pregelatinized starch+water) was sprayed into the fluidized product bed. With reference to Table 24, the moisture level of the formulation was maintained at below 20% by LOD (loss on drying method) at all times during the spraying process. The surface area of the resulting formulation was greater than 10 square meters per gram.

TABLE 24

| Time (min) | Spray Rate (g/min) | Pump Speed (rpm) | Inlet Air (SCFM) | Inlet Temp (° C.) | Product Temp (° C.) | Atom Air (psi) | Exhaust Temp (° C.) | LOD (%) |
|---|---|---|---|---|---|---|---|---|
| 0 | — | — | 149 | 55.4 | 39.8 | — | 44.5 | 12.05 |
| 10 | 86.1 | 31 | 153 | 70.3 | 36.0 | 65.0 | 39.6 | 12.44 |
| 20 | 88.2 | 31 | 152 | 70.1 | 32.0 | 64.9 | 35.4 | 13.01 |
| 30 | 87.9 | 31 | 146 | 69.8 | 30.0 | 65.1 | 36.6 | 13.38 |
| 40 | 90.1 | 31 | 153 | 70.0 | 28.9 | 64.8 | 30.6 | 13.80 |
| 50 | 85.2 | 31 | 151 | 70.0 | 28.6 | 65.1 | 29.8 | 14.36 |
| 60 | 87.5 | 31 | 144 | 70.0 | 28.2 | 65.1 | 28.9 | 15.03 |
| 70 | 89.0 | 31 | 153 | 72.5 | 28.1 | 65.1 | 28.4 | 16.49 |
| 80 | 87.0 | 31 | 145 | 75.9 | 28.4 | 65.1 | 28.3 | 16.34 |
| 90 | 88.7 | 31 | 153 | 78.5 | 28.9 | 65.1 | 28.5 | 17.25 |
| 100 | 94.0 | 31 | 149 | 80.3 | 29.2 | 64.9 | 28.5 | 17.43 |
| 110 | 82.5 | 31 | 153 | 80.2 | 29.2 | 65.1 | 28.4 | 19.60 |
| 120 | 78.3 | 25 | 152 | 79.9 | 30.0 | 64.9 | 28.9 | 19.08 |
| 130 | 66.4 | 25 | 153 | 79.9 | 29.2 | 64.9 | 28.4 | 19.24 |
| 141 | 66.3 | 25 | 152 | 79.8 | 29.8 | 65.1 | 28.6 | 19.29 |
| 150 | 66.1 | 25 | 153 | 80.2 | 29.7 | 64.9 | 28.7 | 18.44 |
| 160 | 65.7 | 25 | 152 | 80.1 | 29.6 | 65.1 | 28.5 | 18.43 |
| 170 | 66.1 | 25 | 153 | 80.1 | 30.0 | 65.1 | 28.8 | 18.85 |
| 181 | 57.7 | 25 | 152 | 79.9 | 29.4 | 64.8 | 28.4 | — |
| 191 | 76.9 | 25 | 154 | 80.0 | 29.4 | 65.0 | 28.3 | 16.70 |
| 200 | 63.9 | 25 | 153 | 80.0 | 30.2 | 65.0 | 28.7 | 18.64 |
| 210 | — | — | 150 | 74.6 | 31.0 | — | 28.0 | 16.97 |
| 220 | — | — | 150 | 80.7 | 37.1 | — | 31.7 | 14.95 |
| Final LOD = | | | | | | | | 13.30 |

The results showed a reduced surface area between the pre-granulated and post-granulated materials and are depicted in Table 25, Sample 1. Table 25, samples 2 and 3 also show a surface area of over 10 m²/g, which corresponds to rapid immediate release formulation characteristics as described herein. The difference in granule particle surface area is nearly two orders of magnitude over granules that were prepared with increased water as measured by LOD %.

TABLE 25

| | Sample | | |
|---|---|---|---|
| | Sample 1 BET Surface Area (m²/g) | Sample 2 BET Surface Area (m²/g) | Sample 3 BET Surface Area (m²/g) |
| Pre-granulation (API + ProSolv) | 28.87 | 28.87 | 28.87 |
| Post_Granulation | 11.85 | 14.03 | 10.18 |
| PTL_Report_Number | 19005 | 19005 | 19005 |

A significant increase in particle surface area corresponded to a reduction in particle size. Tablets with higher granular surface area had a faster dissolution rate when compared to tablets prepared with a lower granular surface area per unit weight.

Calcium stearate and sodium stearyl fumarate were added as lubricants. The quantity used in the formula are beyond the quantities recommended in the art (e.g., Handbook of Pharmaceutical Excipients fifth edition); 0.5% w/w of sodium stearyl fumarate or 2.4% w/w of calcium stearate was used.

Example 10

A ferric citrate tablet was produced for clinical study as described above. The quantities of tablet components used are depicted in Table 26.

TABLE 26

| Material Description | Target kg/Batch | % w/w Individual Tablet |
|---|---|---|
| Ferric Citrate | 14.89 | 87.6 |
| Pregelatinized Starch | 1.70 | 10.0 |
| Calcium Stearate | 0.406 | 2.4 |
| Purified Water | 15.30 | N/A |
| Core Tablet Total | 17.00 | 100.0 |
| Opadry Purple | 0.51 | 15.0 |
| Purified Water | 2.89 | 85.0 |
| Coated Tablet Total | 17.5 | 100.0 |

Pregelatinized starch was sprayed into a chamber maintained at inlet temperature and product temperature. The LOD % water at every stage of preparation was maintained under 20%. The parameters used during the formulation are disclosed in Table 27.

TABLE 27

| Time (min) | Spray Rate (g/min) | Pump Speed (rpm) | Inlet Air (SCFM) | Inlet Temp (° C.) | Product Temp (° C.) | Atom Air (psi) | LOD (%) | Exhaust Temp (° C.) |
|---|---|---|---|---|---|---|---|---|
| 0 | — | 38 | 150 | 61.5 | 42.6 | 60 | 11.24 | 41.3 |
| 10 | 107.6 | 38 | 151 | 63.0 | 31.3 | 60 | 12.4 | 34.5 |
| 20 | 109.1 | 38 | 151 | 63.1 | 27.1 | 60 | 13.32 | 29.5 |
| 30 | 109.5 | 38 | 150 | 63.0 | 26.1 | 60 | 14.37 | 27.5 |
| 40 | 109.5 | 38 | 151 | 63.0 | 25.5 | 60 | 15.64 | 26.4 |
| 50 | 109.6 | 38 | 151 | 62.9 | 25.3 | 60 | 16.99 | 25.7 |
| 60 | 109.5 | 38 | 152 | 69.4 | 25.9 | 60 | 17.66 | 25.5 |
| 71 | 109.9 | 38 | 153 | 72.8 | 26.9 | 60 | 19.35 | 26.3 |
| 80 | 94.7 | 30 | 153 | 72.3 | 26.9 | 60 | 17.05 | 26.3 |
| 90 | 91.0 | 35 | 151 | 71.7 | 27 | 60 | 19.66 | 26.3 |
| 100 | 88.5 | 30 | 152 | 72.1 | 27.1 | 60 | 19.57 | 26.3 |
| 110 | 81.7 | 30 | 150 | 73.3 | 27.4 | 60 | 18.88 | 26.4 |
| 120 | 85.7 | 33 | 153 | 73.2 | 27.7 | 60 | 16.39 | 26.6 |
| 130 | 97.9 | 35 | 149 | 72.4 | 27.4 | 60 | 18.87 | 26.5 |
| 141 | 94.5 | 33 | 152 | 72.0 | 27.4 | 60 | 18.78 | 26.3 |
| 150 | 93.3 | 34 | 153 | 71.9 | 27.3 | 60 | 18.62 | 26.3 |
| 160 | 93.4 | 34 | 152 | 71.8 | 27.5 | 60 | 18.30 | 26.3 |
| 170 | 95.6 | 34 | 154 | 72.2 | 27.5 | 60 | 19.49 | 26.4 |
| 180 | — | — | 151 | 71.9 | 29.5 | — | 16.71 | 26.8 |

The targeted peak moisture between 19-20% (LOD) was achieved with a moisture content of 19.66% (LOD). Table 28 and Table 29 summarize the physical properties after the granulation step and after the tableting and drying steps.

TABLE 28

| Granulation Characteristics | |
|---|---|
| ScreenSize | % Retained |
| 35_(500 μm) | 0.0 |
| 45_(355 μm) | 1.3 |
| 60_(250 μm) | 11.1 |
| 80_(180 μm) | 16.2 |
| 120_(125 μm) | 19.4 |
| 170_(90 μm) | 16.0 |
| 230_(63 μm) | 16.3 |
| Pan | 18.8 |

TABLE 29

| Final blend (post-tableting and drying) characteristics | |
|---|---|
| Bulk_Density_(g/ml) | 0.460 |
| Tapped_Density_(g/ml) | 0.566 |

TABLE 29-continued

Final blend (post-tableting and drying) characteristics

| | |
|---|---|
| Hausner_Ratio | 1.23 |
| Carr_Index | 19 |

Table 30 and Table 31 summarize the final blend characteristics of the formulations.

TABLE 30

Final Blend Characteristics

| Screen_Size | % Retained |
|---|---|
| 35_(500 μm) | 0.0 |
| 45_(355 μm) | 0.8 |
| 60_(250 μm) | 10.8 |
| 80_(180 μm) | 16.6 |
| 120_(125 μm) | 20.3 |
| 170_(90 μm) | 17.2 |
| 230_(63 μm) | 15.6 |
| Pan | 17.0 |

TABLE 31

Test Results

| | |
|---|---|
| Bulk_Density_(g/ml) | 0.436 |
| Tapped_Density_(g/ml) | 0.573 |
| Hausner_Ratio | 1.31 |
| Carr_Index | 24 |

TABLE 32

| Attribute_or_Setting | Start | Middle | End |
|---|---|---|---|
| Press_Main_Force(kN) | 9.9 | 9.9 | — |
| Press_Pre_Force_(kN) | 3.5 | 4.0 | — |
| Press_Speed_(rpm) | 28.69 | 28.69 | — |
| Friability_(%) | 0.2 | — | — |
| Disintegration(seconds) | 88 | 95 | 105 |

TABLE 33

| Characteristic | Weight | Thickness | Hardness |
|---|---|---|---|
| Mean | 1161 | 7.709 | 15.7 |
| Standard_Deviation | 9.39 | 0.029 | 1.13 |
| Min_Individual | 1150 | 7.680 | 13.8 |
| Max_Individual | 1186 | 7.800 | 18.0 |
| RSD | 0.81 | 0.38 | 7.20 |
| Cpk | 1.88 | 2.21 | 1.26 |

The compression data demonstrates that the subject formulation and process were capable of producing a robust tablet with rapid disintegration. The Cpk value for individual tablet weight demonstrates the process was capable of consistently producing tablets within a specification of ±5% of target. The tablet thickness and tablet hardness met the specified acceptance criteria.

Coating and Drying Operating Parameters:

The Opadry® coating suspension was prepared to 15% solids content by weight. The theoretical weight gain for the subject batch was 3%. The film coating was a non-functional component used for aesthetics purposes only and therefore the actual weight gain was not critical to drug performance. The process sprayed to the theoretical quantity of coating suspension and not to a specific weight gain (an efficiency factor was not used). The average coated tablet weight post drying was 1110 mg.

The operating parameters in Table 34 were used during the coating process:

TABLE 34

| Time (min.) | AirFlow (cfm) | Inlet Temp (° C.) | Dew Point (° C.) | Exhaust Temp (° C.) | Spray Rate (g/min) | Atom Air (psi) | Pan Speed (rpm) |
|---|---|---|---|---|---|---|---|
| 0 | 308 | 55.0 | 4.9 | 33.2 | 45 | 37 | 10 |
| 15 | 317 | 46.0 | 5.6 | 36.4 | 48 | 37 | 10 |
| 30 | 307 | 45.1 | 6.3 | 37.3 | 44 | 37 | 10 |
| 45 | 309 | 50.4 | 7.6 | 34.6 | 40 | 37 | 10 |
| 60 | 307 | 44.4 | 7.6 | 36.7 | 51 | 37 | 10 |
| 75 | 310 | 52.9 | 7.5 | 37.3 | 53 | 37 | 10 |

The operating parameters in Table 35 were used during the final tablet drying process:

TABLE 35

| Time (min) | Air Flow (cfm) | Inlet Temp (° C.) | DewPoint (° C.) | Exhaust Temp (° C.) | % Water (LOD) |
|---|---|---|---|---|---|
| 0 | 503 | 70.2 | 7.3 | 50.6 | 13.19 |
| 15 | 504 | 69.7 | 7.2 | 63.3 | 11.93 |
| 30 | 494 | 69.6 | 7.2 | 65.4 | 11.33 |
| 45 | 502 | 69.6 | 7.0 | 66.3 | 11.14 |
| 60 | 500 | 70.4 | 6.8 | 67.0 | 10.14 |
| 75 | 502 | 80.1 | 7.0 | 73.0 | 9.73 |
| 90 | 501 | 80.2 | 7.0 | 74.5 | 9.59 |
| 105 | 505 | 79.7 | 6.8 | 75.4 | 8.96 |
| 120 | 509 | 81.1 | 6.8 | 75.7 | 8.78 |
| 135 | 510 | 81.2 | 6.6 | 76.2 | 8.21 |
| 150 | 505 | 81.1 | 6.7 | 76.5 | 7.88 |

The dissolution profiles demonstrate that higher moisture levels in the tablet can reduce the dissolution rate over time. Tablets with high moisture content exposed to high temperature experienced accelerated reductions in dissolution rate. The post-dried tablet, which had an end moisture content of 8.84% (LOD), did not experience the same reduction in dissolution rate. The tablets containing high moisture level and calcium stearate experienced the greatest reduction in dissolution rate.

The core and coated tablets containing calcium stearate had slightly higher moisture contents (~15% LOD) when compared to the core tablets containing sodium stearyl fumarate (~14% LOD). Without wishing to be held to a particular theory or mode of action, this could be contributing to the difference in the observed dissolution rates. The final moisture content of the tablet and moisture in the tablet during manufacture appear to contribute to the immediate release characteristics and long term stability of the tablet.

The one month stability profile of pre-dried and post-dried tablets' stability were measured. The stability included both 25° C./60% RH and 40° C./75% RH conditions. All samples were placed into HDPE bottles (0.025" wall thickness) with a foil induction seal cap, and a small portion of the study included bottles with desiccants. The following charts summarize the informal stability data.

Figure 10:
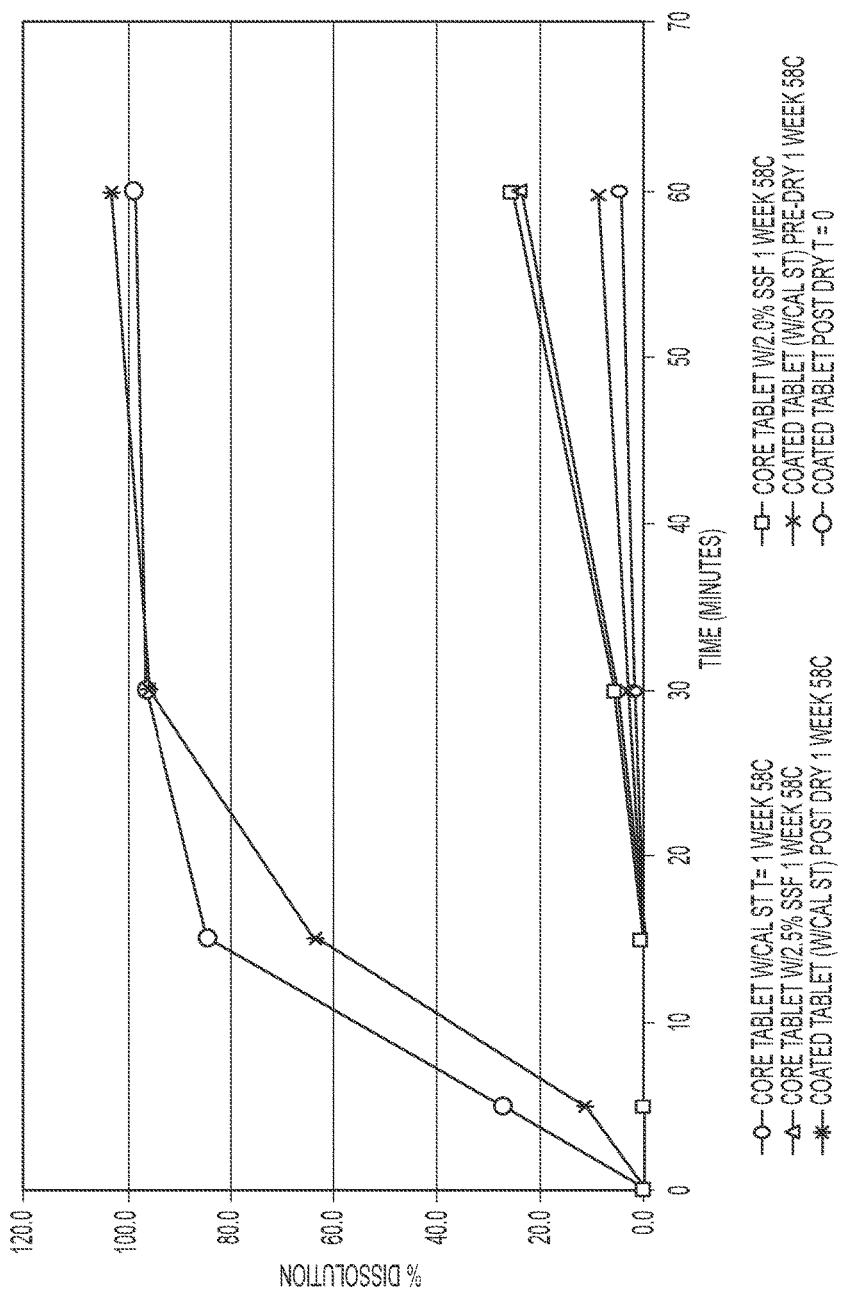
FIG. 10 shows the dissolution time for different tablets that were pre-dried and post-dried.

With reference to FIG. 10, the immediate dissolution rate (greater than 80% at 60 minutes after administration) of tablets exposed to the post-dry process was maintained. The dissolution rate reduced dramatically after one week at in the absence of the post-dry process.

Example 11: Clinical Study of Ferric Citrate Dosage Forms

A protocol for performing clinical studies of a ferric citrate drug formulation as described above is provided as follows.

The protocol includes a 6-Week Feasibility Trial of a New Formulation of KRX-0502 (Ferric Citrate) in Patients with End-Stage Renal Disease (ESRD). The objective of the study is to determine the potential efficacy as a dietary phosphate binder and tolerability of KRX-0502 (ferric citrate) in controlling and managing serum phosphorus levels in patients with end-stage renal disease (ESRD) and monitoring the change in serum phosphorus from baseline to end of treatment after a four week treatment period.

The study design includes conducting the study of the drug in patients with ESRD on thrice weekly hemodialysis. Approximately 24 patients (twelve diabetic and twelve non-diabetic patients) will be initiated on study drug over two to three weeks.

The study consists of five periods: Screening, Washout, Study Drug Initiation, Treatment, and Final Visit. The two-week washout period is immediately followed by a six-week treatment period. The duration of the clinical trial is approximately three to four months with approximately two to three weeks being allocated for patient screening, washout, and initiation of the study drug.

The study population includes all ESRD patients on thrice weekly hemodialysis for at least three months prior to the Study Drug Initiation Visit (Visit 3) who are currently taking at least three tablets/capsules per day of calcium acetate, calcium carbonate, lanthanum carbonate or sevelamer (hydrochloride or carbonate) or any combination of these agents will be eligible for enrollment. Approximately twelve patients will be diabetic and twelve patients will be non-diabetic. Approximately 24 to 48 patients will be screened to initiate approximately 24 patients on study drug. All patients will be recruited from 2-4 sites.

The study for the drug administration includes initiating approximately 24 patients on KRX-0502 (ferric citrate) following a two week washout period from their current phosphate binder and monitoring the serum phosphorus level during the study. The target level of serum phosphorus is approximately 3.5 to 5.5 mg/dL. The serum phosphorus levels will be checked weekly during the washout period and during the visits 4, 5, 6, and at the Final Visit (Visit 7) of the treatment period.

The KRX-0502 dosage is determined by initiating all patients on the study drug with a fixed dosage of 6 tablets per day with each tablet of ferric citrate containing 210 mg of ferric iron as ferric citrate (approximately 1260 mg of ferric iron as ferric citrate) and titrating the blood samples of the patients at Visits 4, 5, and 6 as follows:

For a serum phosphorus level from 3.5-5.5 mg/dL of the blood, no action is required, for a rise to >5.6-6.9 mg/dL, the drug dosage is increased by one tablet per day and for a rise to 6.9 mg/dL, the dosage is increased to 3 tablets per day to a maximum of 12 tablets/day.

Patients take the study drug orally with meals or snacks or within one hour after their meals or snacks. Patients are instructed not to take the study drug if greater than one hour has passed since the ingestion of their meals or snacks. Some patients can require a different distribution in tablets in a given day due to snacks or missed meals. For example, if the patient is receiving a starting dose of 6 g/day that patient can be taking 2 tablets with breakfast, 2 with lunch, and 2 with dinner and can be switched to 1 with breakfast, 1 with a morning snack, 1 with lunch, 1 with a afternoon snack and 2 with dinner if diet dictates.

The second phase of the study in the statistical plan, the drug efficacy study, assesses the tolerability and safety of the study drug. Drug safety is assessed by recording and monitoring adverse events, reviewing concomitant medication use, conducting brief physical examinations (weight, blood pressure and heart rate), and obtaining sequential blood chemistries (including serum phosphorus, serum calcium and selected iron parameters) and rates of adverse events and changes in laboratory parameters.

While several particular forms of the disclosure have been illustrated and described, it will be apparent that various modifications and combinations of the disclosure detailed in the text and drawings can be made without departing from the spirit and scope of the disclosure. For example, references to materials of construction, methods of construction, specific dimensions, shapes, utilities or applications are also not intended to be limiting in any manner and other materials and dimensions could be substituted and remain within the spirit and scope of the disclosure.

What is claimed is:

1. A method for the prophylaxis or treatment of hyperphosphatemia comprising administering to a patient in need thereof a ferric citrate tablet, wherein the ferric citrate tablet comprises:
   (a) a core comprising approximately 90% to approximately 92% by weight of ferric citrate, approximately 4.5% to approximately 30% by weight of pregelatinized starch, and approximately 0.5% to approximately 3% by weight of a lubricant; and
   (b) a coating,
   wherein the tablet has a friability equal or less than 1% w/w, and wherein at least 80% of the ferric citrate in the tablet is dissolved in less than or equal to 60 minutes as measured by test method USP <711>, and the moisture content of the tablet is less than 10% by loss on drying (LOD).

2. The method of claim 1, wherein the lubricant is calcium stearate.

3. The method of claim 1, wherein the tablet comprises approximately 1000 mg of ferric citrate.

4. A method for the prophylaxis or treatment of hyperphosphatemia comprising administering to a patient in need thereof a ferric citrate tablet containing approximately 210 mg of ferric iron, wherein the ferric citrate tablet comprises:
   (a) a core comprising approximately 87.6% by weight of ferric citrate, approximately 10% by weight of pregelatinized starch, and approximately 2.4% by weight of calcium stearate; and
   (b) a coating,
   wherein the tablet has a friability equal or less than 1% w/w and a disintegration time less than 15 minutes, and wherein at least 80% of the ferric citrate in the tablet is dissolved in less than or equal to 60 minutes as measured by test method USP <711>, and the moisture content of the tablet is 8.84% (LOD).

5. A method for the prophylaxis or treatment of hyperphosphatemia comprising administering to a patient in need thereof a ferric citrate tablet, wherein the ferric citrate tablet comprises:
   (a) a core comprising approximately 90% to approximately 92% by weight of ferric citrate, approximately 4.5% to approximately 30% by weight of pregelatinized starch, and approximately 0.5% to approximately 3% by weight of a lubricant; and (b) a coating,
wherein the tablet has a friability equal or less than 1% w/w, and wherein at least 80% of the ferric citrate is dissolved in less than or equal to 60 minutes as measured by test method USP <711>, and the moisture content of the tablet is between 5% to 10% by LOD.

6. The method of claim 5, wherein the lubricant is calcium stearate.

7. The method of claim 5, wherein the tablet comprises approximately 1000 mg of ferric citrate.

8. A method for the prophylaxis or treatment of hyperphosphatemia comprising administering to a patient in need thereof a ferric citrate tablet, wherein the ferric citrate tablet comprises:
(a) a core comprising approximately 90% to approximately 92% by weight of ferric citrate, approximately 1.5% to approximately 15% by weight of pregelatinized starch, and approximately 0.5% to approximately 3% by weight of a lubricant; and
(b) a coating,
wherein the tablet has a friability equal or less than 1%, and wherein at least 80% of the ferric citrate in the tablet is dissolved in less than or equal to 60 minutes as measured by test method USP<711>, and the moisture content of the tablet is between 5% to 10% by LOD.

9. The method of claim 8, wherein the lubricant is calcium stearate.

10. The method of claim 8, wherein the tablet comprises approximately 1000 mg of ferric citrate.

11. A method for controlling serum phosphorus levels in an end-stage renal disease patient on hemodialysis comprising administering to the patent a ferric citrate tablet, wherein the ferric citrate tablet comprises:
(a) a core comprising approximately 90% to approximately 92% by weight of ferric citrate, approximately 4.5% to approximately 30% by weight of pregelatinized starch, and approximately 0.5% to approximately 3% by weight of a lubricant; and
(b) a coating,
wherein the tablet has a friability equal or less than 1% w/w, and wherein at least 80% of the ferric citrate in the tablet is dissolved in less than or equal to 60 minutes as measured by test method USP <711>, and the moisture content of the tablet is less than 10% by loss on drying (LOD).

12. The method of claim 11, wherein the lubricant is calcium stearate.

13. The method of claim 11, wherein the tablet comprises approximately 1000 mg of ferric citrate.

14. A method for controlling serum phosphorus levels in an end-stage renal disease patient on hemodialysis comprising administering to the patent a ferric citrate tablet containing approximately 210 mg of ferric iron, wherein the ferric citrate tablet comprises:
(a) a core comprising approximately 87.6% by weight of ferric citrate, approximately 10% by weight of pregelatinized starch, and approximately 2.4% by weight of calcium stearate; and
(b) a coating,
wherein the tablet has a friability equal or less than 1% w/w and a disintegration time less than 15 minutes, and wherein at least 80% of the ferric citrate in the tablet is dissolved in less than or equal to 60 minutes as measured by test method USP <711>, and the moisture content of the tablet is 8.84% (LOD).

15. A method for controlling serum phosphorus levels in an end-stage renal disease patient on hemodialysis comprising administering to the patent a ferric citrate tablet, wherein the ferric citrate tablet comprises:
(a) a core comprising approximately 90% to approximately 92% by weight of ferric citrate, approximately 4.5% to approximately 30% by weight of pregelatinized starch, and approximately 0.5% to approximately 3% by weight of a lubricant; and
(b) a coating,
wherein the tablet has a friability equal or less than 1% w/w, and wherein at least 80% of the ferric citrate is dissolved in less than or equal to 60 minutes as measured by test method USP <711>, and the moisture content of the tablet is between 5% to 10% by LOD.

16. The method of claim 15, wherein the lubricant is calcium stearate.

17. The method of claim 15, wherein the tablet comprises approximately 1000 mg of ferric citrate.

* * * * *